United States Patent
Rogel et al.

(10) Patent No.: US 9,671,384 B2
(45) Date of Patent: Jun. 6, 2017

(54) LOW VOLUME IN-LINE FILTRATION METHOD FOR EVALUATION OF ASPHALTENES FOR HYDROCARBON-CONTAINING FEEDSTOCK

(71) Applicants: Estrella Rogel, Orinda, CA (US); Cesar Ovalles, Walnut Creek, CA (US); Michael Moir, San Ramon, CA (US)

(72) Inventors: Estrella Rogel, Orinda, CA (US); Cesar Ovalles, Walnut Creek, CA (US); Michael Moir, San Ramon, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 199 days.

(21) Appl. No.: 14/567,780

(22) Filed: Dec. 11, 2014

(65) Prior Publication Data
US 2016/0169858 A1 Jun. 16, 2016

(51) Int. Cl.
G01N 33/28 (2006.01)
G01N 1/40 (2006.01)
G01N 30/86 (2006.01)
G01N 30/88 (2006.01)

(52) U.S. Cl.
CPC ..... *G01N 33/2835* (2013.01); *G01N 30/8679* (2013.01); *G01N 2001/4088* (2013.01); *G01N 2030/8854* (2013.01)

(58) Field of Classification Search
CPC .. G01N 1/10; G01N 33/2835; G01N 30/8679; G01N 2001/4088; G01N 2030/8854
See application file for complete search history.

(56) References Cited

U.S. PATENT DOCUMENTS

| | | | | |
|---|---|---|---|---|
| 3,793,189 | A | * | 2/1974 | Corbett ................... C10C 3/005 208/22 |
| 4,595,667 | A | * | 6/1986 | Takase ................... C10G 45/04 502/63 |
| 4,634,680 | A | | 1/1987 | Kingsley |

(Continued)

OTHER PUBLICATIONS

VICI JOUR—Filters and Mobile Phase Filters, VICI AG International, 2013.*

(Continued)

*Primary Examiner* — David Bolduc
(74) *Attorney, Agent, or Firm* — Ryan, Mason & Lewis, LLP

(57) ABSTRACT

Disclosed herein is a method involving the steps of method for determining asphaltene stability in a hydrocarbon-containing sample having solvated asphaltenes therein, the method comprising the steps of: (a) precipitating an amount of asphaltenes from a liquid sample of the hydrocarbon-containing sample having solvated asphaltenes therein with one or more first solvents and capturing the precipitated asphaltenes in one or more low volume filters comprising a porous filter element comprising an area through which a fluid may flow; (b) determining one or more solubility characteristics of the precipitated asphaltenes; and (c) analyzing the one or more solubility characteristics of the precipitated asphaltenes.

28 Claims, 16 Drawing Sheets

(56) References Cited

U.S. PATENT DOCUMENTS

| | | | | |
|---|---|---|---|---|
| 4,843,247 A * | 6/1989 | Yamazoe | | G01N 21/314 250/573 |
| 5,374,350 A * | 12/1994 | Heck | | B01J 21/18 208/143 |
| 5,911,954 A | 6/1999 | Ford et al. | | |
| 6,039,885 A * | 3/2000 | Behar | | B01D 39/2068 210/335 |
| 6,087,662 A * | 7/2000 | Wilt | | G01N 33/2823 250/339.09 |
| 6,197,075 B1 * | 3/2001 | Muir | | C07C 51/414 44/331 |
| 6,773,921 B1 | 8/2004 | Schabron et al. | | |
| 7,790,646 B2 | 9/2010 | Lopez et al. | | |
| 8,273,581 B2 | 9/2012 | Schabron et al. | | |
| 8,367,425 B1 | 2/2013 | Schabron et al. | | |
| 8,492,154 B1 | 7/2013 | Schabron et al. | | |
| 8,530,240 B1 | 9/2013 | Schabron et al. | | |
| 8,628,970 B1 | 1/2014 | Schabron et al. | | |
| 8,658,030 B2 | 2/2014 | Osaheni et al. | | |
| 9,458,389 B1 | 10/2016 | Schabron et al. | | |
| 2003/0211621 A1 * | 11/2003 | Rovani, Jr. | | G01N 29/07 436/55 |
| 2007/0048874 A1 * | 3/2007 | Schabron | | G01N 33/28 436/141 |
| 2007/0056881 A1 * | 3/2007 | Berkowitz | | C10G 1/047 208/435 |
| 2008/0056822 A1 * | 3/2008 | Hall | | E01C 19/176 404/90 |
| 2008/0251418 A1 * | 10/2008 | Francisco | | C10G 1/04 208/44 |
| 2009/0052986 A1 * | 2/2009 | Hall | | E01C 23/065 404/90 |
| 2009/0057196 A1 * | 3/2009 | Leta | | C10B 55/00 208/85 |
| 2009/0159505 A1 * | 6/2009 | Da Costa | | C10G 67/02 208/302 |
| 2009/0163350 A1 * | 6/2009 | Da Costa | | B01D 61/147 502/31 |
| 2009/0242459 A1 * | 10/2009 | Soloveichik | | C10G 21/00 208/213 |
| 2010/0136698 A1 * | 6/2010 | Dadic | | B01L 3/5023 436/43 |
| 2010/0182591 A1 * | 7/2010 | Chambon | | G01N 33/2835 356/51 |
| 2011/0066441 A1 * | 3/2011 | Ovalles | | C10G 75/00 705/1.1 |
| 2011/0098507 A1 * | 4/2011 | Cohrs | | C07F 9/3808 568/14 |
| 2011/0120950 A1 | 5/2011 | Schabron et al. | | |
| 2011/0152136 A1 * | 6/2011 | Hughes | | C09K 8/524 507/232 |
| 2011/0172924 A1 * | 7/2011 | Hughes | | C09K 8/594 702/11 |
| 2011/0198264 A1 | 8/2011 | Tanaka et al. | | |
| 2011/0247964 A1 * | 10/2011 | Den Boestert | | C10G 31/09 208/187 |
| 2011/0278460 A1 * | 11/2011 | Respini | | C10G 75/00 250/340 |
| 2012/0160015 A1 * | 6/2012 | Ovalles | | G01N 30/88 73/61.52 |
| 2013/0067991 A1 * | 3/2013 | Schabron | | G01N 30/461 73/23.37 |
| 2013/0104772 A1 * | 5/2013 | Schabron | | C08L 95/005 106/277 |
| 2013/0124105 A1 * | 5/2013 | Rogel | | G01N 33/2823 702/25 |
| 2013/0124106 A1 * | 5/2013 | Rogel | | G01N 33/2823 702/25 |
| 2013/0312501 A1 | 11/2013 | Dewey et al. | | |
| 2014/0020456 A1 | 1/2014 | Dreyfus et al. | | |
| 2014/0021101 A1 * | 1/2014 | Schabron | | C10G 25/003 208/309 |
| 2014/0021116 A1 | 1/2014 | Ford et al. | | |
| 2014/0130581 A1 * | 5/2014 | Ovalles | | C09K 8/04 73/61.55 |
| 2014/0369889 A1 * | 12/2014 | Mostowfi | | G01N 33/2823 422/82.09 |
| 2014/0375991 A1 * | 12/2014 | Schneider | | G01N 31/16 356/326 |
| 2015/0218461 A1 * | 8/2015 | Schabron | | C10G 33/00 516/9 |
| 2015/0225655 A1 * | 8/2015 | Adams | | C10G 33/04 516/138 |

OTHER PUBLICATIONS

Al-Jarrah, M. F., et al., Fuel Science Technology Int. I, 4, (1986) 249-260.

Alvarez et al. "Modeling, simulation and analysis of heavy oil hydroprocessing in fixed-bed reactors employing liquid quench streams", Applied Catalysis A: General, 2009, v. 361, pp. 1-12.

Barton, A. F. M., *Handbook of Solubility*; CRC Press, 2$^{nd}$ Edition, 1991, pp. 88-93.

Barton, A. F. M., *Handbook of Solubility Parameters and Other Cohesion Parameters*; CRC Press Inc.: Boca Raton, FL, p. 95 (1983).

Barton, A. F. M., *Handbook of Solubility Parameters and other Cohesion Parameters*, CRC Press, USA, 2$^{nd}$ Edition 1991, p. 63.

Barton, A. F. M., *Handbook of Solubility Parameters and Other Cohesion Parameters*, CRC Press, USA, 2$^{nd}$ Edition 1991, pp. 104-107.

Barton, A. F. M., *Handbook of Solubility*; CRC Press, 2nd Edition, 1991, pp. 288-289.

Carbognani, et al., Energy Fuels, 2002, 16, 1348.

Ceballo, et al., Petroleum Science and Technology, 1999, 17, 783.

Chapter 7 Catalyst deactivation in "Studies in Surface Science and Catalysis," vol. 169 (2007) pp. 141-216.

Johnson and Moyse, "Pretreatment of resid FCC feedstocks", Jul. 2004, http://www.digitalrefining.com/article/1000161.

Liaw et al. "Catalytic Hydrotreatment of Coal-Derived Naphtha Using First Row Transition Metal Sulfides", ACS Fuel Preprint, Aug. 1993, pp. 1065-1072: http://web.anl.gov/PCS/acsfuel/preprint%20archive/Files/38_3_CHICAG0_08-93_1065.pdf.

Mariaca-Domanguez et al. "Reactivity of Fluid Catalytic Cracking Feedstocks as a Function of Reactive Hydrogen Content", Petroleum Science and Technology, 2004, vol. 22, Issue 1-2, pp. 13-29.

Matsushita et al. "Relation between relative solubility of asphaltenes in the product oil and coke deposition in residue hydroprocessing", Fuel, 2004, 83, pp. 1669-1674.

McLean and Duddy, "Reactivity Screening of Feedstocks for Catalytic Coal/Oil Co-Processing", ACS Fuel Preprint, Sep. 1986, pp. 169-180: http://web.anl.gov/PCS/acsfuel/preprint%20archive/Files/31_4_ANAHEIM_09-86_0169.pdf.

Mitchell, et al., Fuel, 1973, 52, 151.

Moschopedis, et al.. Fuel, 1971, 50, 34.

Riechardt, C., "Solvents and Solvent Effects in Organic Chemistry" Wiley-Vch Verlag GmbH & Co., Weinheim, Germany, 2004, p. 68.

Rutan et al., L. R. J. Chromatogr., 463, 21, 1989.

Snyder et al., Practical HPLC Method Development, Wiley and sons, 1997, p. 208.

Snyder, et al., "Introduction to Modern Liquid Chromatography." 1997. Wiley, p. 207.

Stanislaus et al. "Pilot Plant Study of the Performance of an Industrial Mo03/Al203 Catalyst in Hydrotreatment of Kuwait Atmospheric Residue", ACS Fuel Preprints, Aug. 1999: http://web.anl.gov/PCS/acsfuel/preprint%20archive/Files/44_4_NEW%200RLEANS_08-99_0827.pdf.

Xu et al., "Catalytic hydrotreatment of coal-derived naphtha", ACS Fuel Preprint, Aug. 1991: http://web.anl.gov/PCS/acsfuel/preprint%20archive/Files/36_4_NEW%20YORK_08-91_1909.pdf.

Yang and Xu, "Characteristics on HDS and HDN kinetics on narrow fractions from residua", ACS Fuel Preprint, Aug. 1998 http://web.anl.gov/PCS/acsfuel/preprint%20archive/Files/43_3_BOSTON_08-98_0751.pdf.

(56) References Cited

OTHER PUBLICATIONS

M.M. Boduszynski et al., "Separation of Solvent-Refined Coal into Solvent-Derived Fractions," Analytical Chemistry, 1982, pp. 372-375, vol. 54, No, 3.

F.P. Burke et al., "Liquid Column Fraction: A Method of Solvent Frationation of Coal Liquefaction and Petroleum Products", Fuel, 1979, pp. 539-541, vol. 28, No. 7.

F.K. Schweighardt et al., "Evaluation of Analytical Techniques for SRC-1 Characterization, Recycle Solvent Studies, and Product Fractionation Studies: Development of SRC-1 Product Analysis," United States Department of Energy Technical Report No. DOE/OR/03054-61—vol.2, Sep. 1983, pp. 250 and 276.

* cited by examiner

LOW VOLUME IN-LINE FILTRATION METHOD FOR EVALUATION OF ASPHALTENES FOR HYDROCARBON-CONTAINING FEEDSTOCK

BACKGROUND OF THE INVENTION

1. Technical Field

The present invention generally relates to a method for evaluating asphaltene content, stability and solubility characteristics of a hydrocarbon-containing feedstock employing a low volume, in-line filtration device.

2. Description of the Related Art

Hydrocarbon materials, such as heavy oils, petroleum residua, coal tars, shale oils, asphalts, or the like can comprise polar core materials, such as asphaltenes, dispersed in lower polarity solvent(s). Intermediate polarity material(s), usually referred to as resin(s), can associate with the polar core materials to maintain a homogeneous mixture of the components.

Refinery processes, including but not limited to, atmospheric or vacuum distillation, visbreaking, hydrocracking, delayed coking, Fluid Coking, Flexicoking, hydrotreatment, delay coker or Eureka process that convert hydrocarbon materials to lighter distillate fuels that require heating for distillation, hydrogen addition, or carbon rejection (coking). However, when using conventional refinery processes, the efficiency of converting such hydrocarbon material may be limited by transition of the hydrocarbon material of homogeneous mixture to a hydrocarbon material of heterogeneous mixture. The transition to the heterogeneous mixture may include the formation of insoluble carbon-rich deposits, including the formation of coke or coke-containing materials. As such, any reduction in carbon deposition, or increase in the distillation yield during the thermal processing of hydrocarbon material can have a significant impact on the manner or economics of hydrocarbon processing.

Asphaltenes are organic heterocyclic macromolecules which occur in crude oils. Under normal reservoir conditions, asphaltenes are usually stabilized in the crude oil by maltenes and resins that are chemically compatible with asphaltenes, but that have lower molecular weight. Polar regions of the maltenes and resins surround the asphaltene while non-polar regions are attracted to the oil phase. Thus, these molecules act as surfactants and result in stabilizing the asphaltenes in the crude. However, changes in pressure, temperature or concentration of the crude oil can alter the stability of the dispersion and increase the tendency of the asphaltenes to agglomerate into larger particles. As these asphaltene agglomerates grow, so does their tendency to precipitate out of solution.

One of the problems encountered in crude oil production and refining is asphaltene precipitation. Generally, unwanted asphaltene precipitation is a concern to the petroleum industry due to, for example, plugging of an oil well or pipeline as well as stopping or decreasing oil production. Also, in downstream applications, asphaltenes are believed to be the source of coke during thermal upgrading processes thereby reducing and limiting yield of residue conversion. In catalytic upgrading processes, asphaltenes can contribute to catalyst poisoning by coke and metal deposition thereby limiting the activity of the catalyst.

Asphaltenes can also cause fouling in, for example, heat exchangers and other equipment in a refinery. Fouling in heat transfer equipment used for streams of petroleum origin can result from a number of mechanisms including chemical reactions, corrosion and the deposit of materials made insoluble by the temperature difference between the fluid and heat exchange wall. The presence of insoluble contaminants may exacerbate the problem: blends of a low-sulfur, low asphaltene (LSLA) crude oil and a high-sulfur, high asphaltene (HSHA) crude, for example, may be subject to a significant increase in fouling in the presence of iron oxide (rust) particulates. Subsequent exposure of the precipitated asphaltenes over time to the high temperatures then causes formation of coke as a result of thermal degradation.

Equipment fouling is costly to petroleum refineries and other plants in terms of lost efficiencies, lost throughput, and additional energy consumption, and, with the increased cost of energy, heat exchanger fouling has a greater impact on process profitability. Higher operating costs also accrue from the cleaning required to remove fouling. While many types of refinery equipment are affected by fouling, cost estimates have shown that the majority of profit losses occur due to the fouling of whole crude oils, blends and fractions in pre-heat train exchangers.

Fouling is generally defined as the accumulation of unwanted materials on the surfaces of processing equipment. In petroleum processing, fouling is the accumulation of unwanted hydrocarbon-based deposits on, for example, heat exchanger surfaces. It has been recognized as a nearly universal problem in design and operation of refining and petrochemical processing systems, and affects the operation of equipment in two ways. First, the fouling layer has a low thermal conductivity. This increases the resistance to heat transfer and reduces the effectiveness of the heat exchangers. Second, as deposition occurs, the cross-sectional area is reduced, which causes an increase in pressure drop across the apparatus and creates inefficient pressure and flow in the heat exchanger.

One of the more common causes of rapid fouling, in particular, is the formation of coke that occurs when crude oil asphaltenes are overexposed to heater tube surface temperatures. The liquids on the other side of the exchanger are much hotter than the whole crude oils and result in relatively high surface or skin temperatures. Certain asphaltenes can precipitate from the oil and adhere to these hot surfaces. Another common cause of rapid fouling is attributed to the presence of salts and particulates. Salts/particulates can precipitate from the crude oils and adhere to the hot surfaces of the heat exchanger. Inorganic contaminants play both an initiating and promoting role in the fouling of whole crude oils and blends. Iron oxide, iron sulfide, calcium carbonate, silica, sodium and calcium chlorides have all been found to be attached directly to the surface of fouled heater rods and throughout the coke deposit.

The cleaning process, whether chemical or mechanical, in petroleum refineries and petrochemical plants often causes costly shutdowns. A majority of refineries practice off-line cleaning of heat exchanger tube bundles based on scheduled time or usage or on actual monitored fouling conditions. Reduction in the extent of fouling will lead to increased run lengths, improved performance and energy efficiency while also reducing the need for costly fouling mitigation options.

In addition, oil refining gives rise to dark heavy high-boiling oil fractions and their mixtures, of which bitumen and heavy fuel oil are made, among other things. The use and storability of these oil raffinates are impaired by the poor solubility or precipitation of asphaltenes in the oil. Thus, susceptibility of the asphaltene components to precipitate determines the stability or storability of the oil, and this depends both on the oil production process used and on the raw materials.

Present methodologies use a vessel connected to a high performance liquid chromatography (HLPC), also known as high pressure liquid chromatography, to evaluate asphaltene precipitation. For example, one such method disclosed in U.S. Patent Application Publication No. 2011020950 involves in-vessel precipitation of asphaltenes using a vessel consisting of an inert non-porous column. These methods have proven to be faster and required less solvent amounts than traditional technologies. However, there are problems associated with the use of a column packed with, for example, Teflon. One such problem is that the filling of a column using, for example, the "tap-fill" method for packing of rigid solids, produces columns that will have different performances because of the difficulties in forming an optimally packed column bed. This, in turn, leads to poorer reproducibility and repeatability of the methodology. In fact, a column prepared by different trained personnel as well as a column prepared by the same personnel produce results with differences of more than 10%.

Another problem is the degradation of the column due to asphaltene adsorption. In addition, the use of a packed column also results in the formation of preferential channels which requires its frequent replacement for a new fresh-packed column. This highly affects repeatability of the methodology because of poorer column-to-column reproducibility. In particular, for processed or paraffinic containing samples, the degradation of the column can be very fast (e.g., less than a month). This, in turn, requires the time-consuming task of preparing a new column which increases capital and operational costs.

Yet another problem is that the use of a column produces very broad peaks when analyzing the solubility profile of the eluted fractions with a liquid chromatography detector. An unexpected result of the present invention is that the use of a filter instead of a column improves significantly the sharpness of the peaks. This is believed to be due to the comparatively lower volume of the filter. For example, a packed column produced by the "tap-fill" method has a high volume which leads to very broad peaks. This reduces the sensitivity and the repeatability of the method due to small signal/noise ratio. In order to keep the peaks as narrow as possible, large flow rates are required when the column is used. This, in turn, limits the type of detectors that can be used with the concomitant reduction in sensitivity. Moreover, even flow rates of the liquid sample as large as 4 mL/min produce peaks that are broader than those obtained by conventional liquid chromatography using much lower flow rates. Also, large flow rates increase solvent consumption.

Finally, another problem is that high volume columns also increase the pressure differential across the HPLC lines, shortening maintenance cycles and lowering life times for pumps and seal pumps.

Another area for improvement arises from the unexpected discovery that the precipitation of the asphaltenes outside the vessel helps in the production of sharper peaks. By using a large sample/precipitant solvent ratio (around 1/10,000), the precipitation occurs instantaneously when the sample enters into contact with the solvent thereby producing a narrow band of asphaltenes, while precipitation in-vessel induces a broader distribution of the asphaltenes within the vessel that also leads to broader peaks. It is undesirable to have broad peaks as they are detrimental for repeatability and limit of detection.

Another important factor in the development of better methodologies to evaluate asphaltene stability is the proper selection of the solvents. Previously, U.S. Pat. No. 8,492,154 ("the '154 patent) disclosed that polarity can be used to select the solvents. It was stated in the '154 patent that the larger the polarity of the solvent the larger the solubility of asphaltenes in the solvent. However, the characterization of a solvent by means of its "polarity" is an unsolved problem as indicated by Riechardt, C., "Solvents and Solvent Effects in Organic Chemistry" Wiley-Vch Verlag GmbH & Co., Weinheim, Germany, 2004, p. 68 ("Riechardt"). In fact, Riechardt points out that the term "polarity" itself has not been precisely defined. According to Riechardt, polarity might be interpreted as: (a) the permanent dipole moment of a compound, (b) its relative permittivity and (c) the sum of all those molecular properties responsible for all the interaction forces between solvent and solute properties.

As examples, Tables 1 and 2 below show two different polarity scales and how they are unable to determine appropriate asphaltene solvents. First, Table 1 shows a polarity scale published by Barton, Allan F. M. "Handbook of Solubility" CRC Press, $2^{nd}$ Edition, 1991, p. 88-93 (see, Tables 7-9), In this scale, polarity is defined by the polar term in the solubility parameter.

Second, Table 2 shows a second so called "polarity" scale defined by Rutan et al., L. R. J. Chromatogr., 463, 21, 1989. This scale cannot be used to select the solvents for asphaltene solubilization. As seen in Tables 1 and 2, "higher polarity" of a solvent does not correlate with higher solubility of asphaltenes in the solvent.

TABLE 1

| Solvent | Polarity | Observation | Reference |
|---|---|---|---|
| Heptane | 0.0 | Does not dissolve asphaltenes | Mitchell, et al., Fuel, 1973, 52, 151. |
| Cyclohexane | 0.0 | Dissolves asphaltenes | Mitchell, et al., Fuel, 1973, 52, 151. |
| Benzene | 0.0 | Dissolves asphaltenes | Mitchell, et al., Fuel, 1973, 52, 151. |
| Toluene | 1.4 | Dissolves asphaltenes | Mitchell, et al., Fuel, 1973, 52, 151. |
| Diethylether | 4.6 | Does not dissolve asphaltenes | Al-Jarrah et al., Fuel Sci. Technol. Int. 1986,4, 249. |
| Tetrahydrofuran | 7.6 | Dissolves asphaltenes | Ceballo, et al., Petroleum Science and Technology, 1999, 17, 783. |
| Pyridine | 7.6 | Dissolves asphaltenes | Mitchell, et al., Fuel, 1973, 52, 151. |
| Ethyl Acetate | 10.6 | Does not dissolve asphaltenes | Carbognani, et al., Energy Fuels, 2002, 16, 1348. |
| Acetone | 12.9 | Does not dissolve asphaltenes | Carbognani, et al., Energy Fuels, 2002, 16, 1348. |
| Acetonitrile | 18.4 | Does not dissolve asphaltenes | Carbognani, et al., E. Energy Fuels, 2002, 16, 1348. |

TABLE 2

| Solvent | Polarity | Observation | Reference |
|---|---|---|---|
| Hexane | −0.14 | Does not dissolve asphaltenes | Mitchell, et al., Fuel, 1973, 52, 151. |
| Cyclohexane | 0.17 | Partially dissolves asphaltenes | Mitchell, et al., Fuel, 1973, 52, 151. |
| Toluene | 2.68 | Dissolves asphaltenes | Mitchell, et al., Fuel, 1973, 52, 151. |
| Diethylether | 3.15 | Does not dissolve asphaltenes | Al-Jarrah et al., Fuel Sci. Technol. Int. 1986,4, 249. |

TABLE 2-continued

| Solvent | Polarity | Observation | Reference |
|---|---|---|---|
| Ethyl Acetate | 4.24 | Does not dissolve asphaltenes | Carbognani, et al., E. Energy Fuels, 2002, 16, 1348. |
| Tetrahydrofuran | 4.28 | Dissolves asphaltenes | Ceballo, et al., Petroleum Science and Technology, 1999, 17, 783. |
| Methylene Chloride | 4.29 | Dissolves asphaltenes | Mitchell, et al., Fuel, 1973, 52, 151. |
| Pyridine | 5.53 | Dissolves asphaltenes | Mitchell, et al., Fuel, 1973, 52, 151. |
| Acetonitrile | 5.64 | Does not dissolve asphaltenes | Carbognani, et al., Energy Fuels, 2002, 16, 1348. |

In the same manner, the use of solvent power or solvent strength without defining a scale to determine the best solvents for asphaltene dissolution is misleading. Solvent power or solvent strength is also ambiguous since its quantification requires a scale. For example, there are scales that apply exclusively to hydrocarbons (see, e.g., Barton, Allan F. M. "Handbook of Solubility" CRC Press, 2nd Edition, 1991, p. 288-289.) and cannot be used for oxygenated agents (e.g., alcohols, ketones, etc.). It is clear that without a scale definition, polarity and solvent power are ill-defined concepts.

Accordingly, it is clear that there is a need to define a proper scale for the successful selection of solvents. The '154 patent uses solubility parameter that comprises three components: dispersion, polar and hydrogen bonding. Each of the components related to a specific type of intermolecular interactions. The '154 patent states that this scale can be used to select which solvents are best to dissolve asphaltenes. However, a larger solubility parameter does not correlate with better solvency of asphaltenes into the solvent as shown below in Table 3.

TABLE 3

| Solvent | $\delta_T$ ($MPa^{0.5}$) | Observation | Reference |
|---|---|---|---|
| Heptane | 15.3 | Does not dissolve asphaltenes | Mitchell, et al., Fuel, 1973, 52, 151. |
| Diethyl ether | 15.8 | Does not dissolve asphaltenes | Al-Jarrah et al., Fuel Sci. Technol. Int. 1986,4, 249. |
| Cyclohexane | 16.8 | Dissolves asphaltenes | Mitchell, et al., Fuel, 1973, 52, 151. |
| Ethyl Acetate | 18.1 | Does not dissolve asphaltenes | Carbognani, et al., Energy Fuels, 2002, 16, 1348. |
| Toluene | 18.2 | Dissolves asphaltenes | Mitchell, et al., Fuel, 1973, 52, 151. |
| Benzene | 18.6 | Dissolves asphaltenes | Mitchell, et al., Fuel, 1973, 52, 151. |
| Tetrahydrofuran | 19.4 | Dissolves asphaltenes | Ceballo, C et al., Petroleum Science and Technology, 1999, 17, 783. |
| Acetone | 20.0 | Does not dissolve asphaltenes | Carbognani, et al., Energy Fuels, 2002, 16, 1348. |
| Methylene chloride | 20.3 | Dissolves asphaltenes | Mitchell, et al., Fuel, 1973, 52, 151. |
| Pyridine | 21.8 | Dissolves asphaltenes | Mitchell, et al., Fuel, 1973, 52, 151. |
| Acetonitrile | 24.4 | Does not dissolve asphaltenes | Carbognani, et al., Energy Fuels, 2002, 16, 1348. |

TABLE 3-continued

| Solvent | $\delta_T$ ($MPa^{0.5}$) | Observation | Reference |
|---|---|---|---|
| Water | 48.0 | Does not dissolve asphaltenes | Moschopedis, et al.. Fuel, 1971, 50, 34 |

An improve method to select the solvents and its order to determine solubility characteristics of the asphaltenes can be based on the dispersion component of the solubility parameter. This component of the solubility parameter takes into account the forces related to the polarizability of the molecules and is commonly associated with their size and shape and it is the predominant interaction force among asphaltenes. The other two components of the solubility parameter, i.e., polar and hydrogen bonding, are minor contributors to asphaltene interactions. This is demonstrated in Table 1 above, where the polarity scale represented by these two contributions cannot be used to select the solvents. In contrast, the dispersion component of the Hansen Parameters (See Barton, A. F. M.; Handbook of Solubility Parameters and Other Cohesion Parameters, Second Edition CRC Pess, USA, 1991, p 104-107) as shown below in Table 4 can be used to select the solvents as it shows the right order in terms of solubility of asphaltenes

TABLE 4

| Solvent | $\delta_d$ ($MPa^{0.5}$) | Observation | Reference |
|---|---|---|---|
| Water | 12.3 | Does not dissolve asphaltenes | Moschopedis, et al., Fuel, 1971, 50, 34 |
| Diethyl ether | 14.5 | Does not dissolve asphaltenes | Al-Jarrah et al., Fuel Sci. Technol. Int. 1986,4, 249. |
| Methanol | 15.1 | Does not dissolve asphaltenes | Carbognani, et al., Energy Fuels, 2002, 16, 1348. |
| Heptane | 15.3 | Does not dissolve asphaltenes | Mitchell, et al., Fuel, 1973, 52, 151. |
| Acetonitrile | 15.3 | Does not dissolve asphaltenes | Carbognani, et al., Energy Fuels, 2002, 16, 1348. |
| Acetone | 15.5 | Does not dissolve asphaltenes | Carbognani, et al., Energy Fuels, 2002, 16, 1348. |
| Ethyl Acetate | 15.8 | Does not dissolve asphaltenes | Carbognani, et al., Energy Fuels, 2002, 16, 1348. |
| Cyclohexane | 16.8 | Dissolves asphaltenes | Mitchell, D et al., Fuel, 1973, 52, 151. |
| Tetrahydrofuran | 16.8 | Dissolves asphaltenes | Ceballo, et al., Petroleum Science and Technology, 1999, 17, 783. |
| Toluene | 18.2 | Dissolves asphaltenes | Mitchell, et al., Fuel, 1973, 52, 151. |
| Methylene chloride | 18.2 | Dissolves asphaltenes | Mitchell, et al., Fuel, 1973, 52, 151. |
| Benzene | 18.4 | Dissolves asphaltenes | Mitchell, et al., Fuel, 1973, 52, 151. |
| Pyridine | 19.0 | Dissolves asphaltenes | Mitchell, et al., Fuel, 1973, 52, 151. |

It would be therefore desirable to provide improved methods for determining, for example, asphaltene content and asphaltene stability, in a hydrocarbon-containing material that can be carried out in a simple, cost efficient and repeatable manner.

SUMMARY OF THE INVENTION

In accordance with one embodiment of the present invention, there is provided a method comprising the steps of:

(a) precipitating an amount of asphaltenes from a liquid sample of the hydrocarbon-containing sample having solvated asphaltenes therein with one or more first solvents and capturing the precipitated asphaltenes in one or more low volume filters comprising a porous filter element comprising an area through which a fluid may flow;

(b) determining one or more solubility characteristics of the precipitated asphaltenes; and (c) analyzing the one or more solubility characteristics of the precipitated asphaltenes.

The method of the present invention advantageously evaluates asphaltene content, stability and solubility characteristics of hydrocarbon-containing feedstock in a more repeatable and reproducible manner as compared to the in-column method. For example, the method of the present invention employing one or more low volume filters comprising a porous filter element significantly improves the sharpness and the symmetry of the peaks obtained when analyzing the solubility profile of the eluted fractions with a liquid chromatography detector whereas the use of a column produces very broad peaks with poor symmetry. Peaks with poor symmetry can result in inaccurate resolution measurements, imprecise quantification, degraded resolution and undetected minor bands in the peak tail and poor reproducibility (see, e.g., Snyder et al., Practical HPLC Method Development, Wiley and sons, 1997, p. 208). Accordingly, the method of the present invention can be carried out in a simple, cost efficient and repeatable manner.

BRIEF DESCRIPTION OF THE DRAWINGS

FIG. 6b shows a blow apart view of the filter housing assembly of FIG. 6a.

DETAILED DESCRIPTION OF THE PREFERRED EMBODIMENTS

Figure 1:
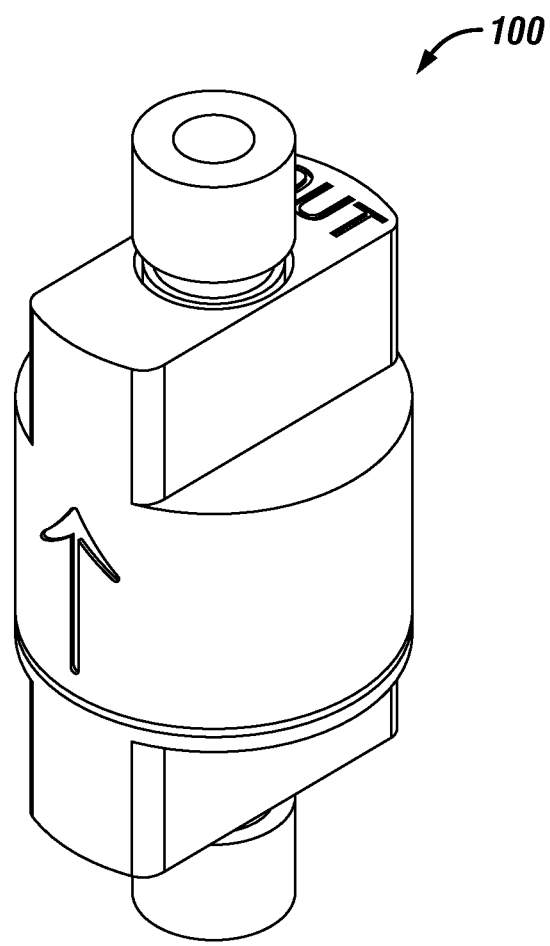
FIG. 1 shows one embodiment of a filter housing assembly for use in the present invention as assembled.

In one embodiment, a method of the present invention involves (a) precipitating an amount of asphaltenes from a liquid sample of the hydrocarbon-containing sample having solvated asphaltenes therein with one or more first solvents and capturing the precipitated asphaltenes in one or more low volume filters comprising a porous filter element comprising an area through which a fluid may flow; (b) determining one or more solubility characteristics of the precipitated asphaltenes; and (c) analyzing the one or more solubility characteristics of the precipitated asphaltenes.

Generally, the source of the hydrocarbon-containing feedstock may be any source wherefrom a hydrocarbon crude may be obtained, produced, or the like. The source may be one or more producing wells in fluid communication with a subterranean oil reservoir. The producing well(s) may be under thermal recovery conditions, or the producing well(s) may be in a heavy oil field where the hydrocarbon crude or oil is being produced from a reservoir having a strong water-drive.

In one embodiment, the hydrocarbon-containing feedstock sample includes any heavy hydrocarbons such as heavy crude oil, heavy hydrocarbons extracted from tar sands, commonly called tar sand bitumen, such as Athabasca tar sand bitumen obtained from Canada, heavy petroleum crude oils such as Venezuelan Orinoco heavy oil belt crudes, Boscan heavy oil, Hamaca crude oil, heavy hydrocarbon fractions obtained from crude petroleum oils, particularly heavy vacuum gas oils, vacuum residuum as well as petroleum tar, tar sands and coal tar. Other examples of heavy hydrocarbon feedstocks which can be used are oil shale, shale, coal liquefaction products and the like.

In another embodiment, the hydrocarbon-containing feedstock sample includes any solid hydrocarbon-containing deposit such as asphaltene solids from, e.g., refinery production preparation or an oil facility.

In another embodiment, the hydrocarbon-containing feedstock sample includes any processed sample, such as, for example, heavy cycle gas oil (HCGO), LC Fining™ products, fluid catalytic cracking (FCC) products and the like. In one embodiment, the hydrocarbon-containing feedstock sample is a refinery stream.

In one embodiment, a liquid sample of a hydrocarbon-containing feedstock having solvated asphaltenes therein is provided. As one skilled in the art will readily understand, it may be necessary to add a solvent to the hydrocarbon-containing feedstock in order for the sample to be sufficiently fluid enough to be passed through the one or more low volume filters. Useful solvents include any solvent in which the hydrocarbon-containing feedstock sample is soluble or which is capable of allowing the hydrocarbon-containing feedstock sample to be sufficiently fluid to be passed through the one or more low volume filters. Representative examples of such solvents include one or more chlorinated hydrocarbon solvents, one or more aromatic hydrocarbon solvents, one or more ether solvents, one or more alcohol solvents and the like and mixtures thereof. Suitable chlorinated hydrocarbon solvents include, but are not limited to, dichloromethane, 1,2-dichloroethane, chloroform, carbon tetrachloride and the like and mixtures thereof. Suitable aromatic hydrocarbon solvents include, but are not limited to, benzene, toluene, xylene and the like and mixtures thereof. Suitable ether solvents include tetrahydrofuran, and like. As one skilled in the art will readily understand, asphaltenes are partially or totally insoluble in, for example, ether solvents such as diethylether, dioxane and the like and mixtures of thereof, and alcohol solvents including low molecular weight aliphatic alcohols such as methanol, ethanol, isopropanol and the like and mixtures thereof. Accordingly, in order to dissolve the asphaltenes, these solvents should be used as part of a blend, e.g., a blend where the dispersion component of the solubility parameter of the blend is such that it can dissolve asphaltenes. In one embodiment, the sample solution can be prepared from about 10 to about 50 wt. % solution of the hydrocarbon-containing feedstock sample in the solvent(s).

In general, an amount of asphaltenes from the liquid sample of the hydrocarbon-containing sample having solvated asphaltenes therein is precipitated with one or more first solvents and then the precipitated asphaltenes are captured in one or more low volume filters comprising a porous filter element comprising an area through which a fluid may flow. Useful one or more first solvents are typically alkane mobile phase solvent(s) and can be determined by one skilled in the art. In one embodiment, the alkane mobile phase solvent is n-heptane. However, other alkane mobile phase solvents such as, for example, n-pentane or n-hexane may be used.

As one skilled in the art will readily appreciate, a solution of the one or more first solvents and liquid sample are passed through the one or more low volume filters for a time period sufficient to elute the alkane soluble fraction, commonly known as maltenes or petrolenes, while the alkane insoluble fraction, i.e., the precipitated asphaltenes, from the hydrocarbon-containing feedstock sample are captured on the one or more low volume filters.

In general, the one or more low volume filters for use in the method of the present invention can be any suitable one or more low volume filters for separation of particles and/or molecules in a liquid sample. Suitable low volume filters for use herein include those that are commercially available from such sources as, for example, Restek, (State College, Pa.), Idex Health & Science, (Oak Harbor, Wash.), and Phenomenex, (Torrance, Calif.), or those disclosed in, for example, U.S. Pat. No. 5,911,954, and U.S. Patent Application Publication Nos. 20130312501 and 20140021116, the contents of which are incorporated by reference herein. The term "low volume" as used herein shall be understood to mean the volume of the void in the filter where no filter material is present. A suitable low volume filter will have a volume of less than 100 µL, e.g., from about 1 µL to about a 100 µL or from about to 1 µL to about 10 µL.

The one or more low volume filters can be made of low surface energy materials such as, for example, stainless steel, gold, titanium, silver, gold coated stainless steel, titanium coated stainless steel or silver coated stainless steel, carbon composite, nickel-containing alloys such as Hastelloy® Alloy (available from Haynes International), polyaryletherketones, polytetrafluoroethylene, and the like. As one skilled in the art will readily appreciate, and as discussed below, the elements forming the one or more low volume filters can be made of the same or different material. In one preferred embodiment, the low volume filters comprising a porous filter element is generally circular in shape.

The one or more low volume filters will be able to operate at pressures up to about 15,000 psi. In one embodiment, the one or more low volume filters will operate at pressures ranging from about 14 psi to about 15,000 psi. The one or more low volume filters can operate at room temperature or can be subjected to a temperature up to about 350° C., e.g., a temperature ranging from about 18° C. to about 350° C.

The porous filter element of the low volume filters will comprise an area through which a fluid may flow. As used herein, the term "porous filter element" shall be understood to mean a porous filter element constructed from a woven or non-woven material and excludes a packed media filter. As one skilled in the art will readily appreciate, non-woven material can be a porous material having an area through which a fluid can flow, such as sintered metal particles formed into the porous filter element. In general, the porous filter element will ordinarily have an average pore diameter less than about 10 microns, e.g., an average pore diameter ranging from 0.1 to about 10 microns. In one embodiment, the porous filter element will have an average pore diameter ranging from about 0.1 to about 5 microns. In one preferred embodiment, the porous filter element will have an average pore diameter less than about 1 microns, e.g., an average pore diameter ranging from 0.2 to about 1 microns.

Figure 2:
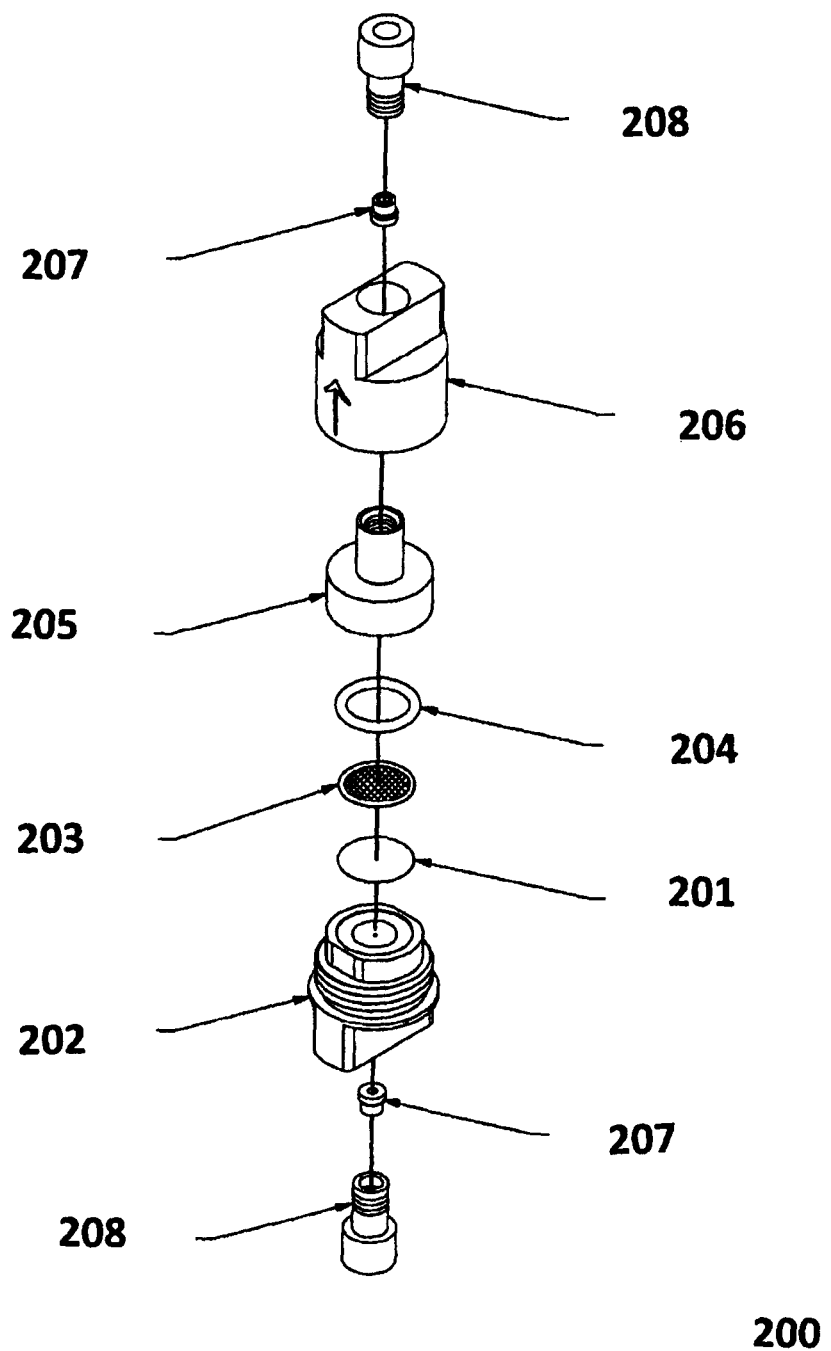
FIG. 2 shows an exploded view an embodiment of a filter housing assembly for use in the present invention with internal elements exposed.

In one embodiment, FIG. 1 illustrates the compact nature of a low volume filter 100 for use in the present invention as well as its simple means of assembly. FIG. 2 shows the elements of one embodiment of the low volume filters of the present invention. A filter element 201 will be sandwiched between inlet filter housing 202 and porous filter element 203. The porous filter element 203, while porous in the central region may be solid along its perimeter. Typically, this porous filter element does not adsorb sample elements, nor is there an associated depth of material to absorb sample. Further the porous filter element allows a uniform flow through the filter into the chamber downstream therefrom due to the uniformity of the filter. Another benefit of the porous filter element is that there is likely to be less flow impedance over the exposed surface of the filter element.

Upon the perimeter of the filter is seated an O-ring 204 or gasket which seals the filter to the O-ring retaining element 205, which is keyed to prevent it from rotating relative to the inlet filter housing 202. The O-ring retainer 205 is threaded to receive a properly threaded outlet fitting. The outlet filter housing 206 is threaded so as to allow it to mate with outlet filter housing 202. As the two halves of the filter housing 202 and 206 are tightened together, they compress the O-ring 204 and seal the assembly. As the O-ring retainer is not threaded, but is keyed to the inlet filter housing 202 it remains fixed relative to the inlet filter housing 202 but allows the outlet filter housing 206 to rotate freely relative thereto during the assembly. This design makes it impossible for the filter element 201 to be rotated during the assembly process, thereby ensuring a fully assembled low volume filter housing assembly 200 whose integrity has not been compromised by possible tearing or cracking of the filter element while the assembly is sealed.

The assembled low volume filter housing assembly may then be placed in-line with a chromatography or other flowing system as discussed below by connecting tubing from the upstream source to the inlet filter housing by means of a ferrule 207 and a fitting 208. A corresponding ferrule 207 and fitting 208 may be used on the outlet side through which the fluid will be delivered downstream of the filter. In an alternate embodiment of the invention, particularly relevant to lower pressure systems, the filter housings 202 and 206 may be threaded so as to receive coned inlet and outlet fittings rather than the flangeless fittings 408 and accompanying ferrules 207 shown in FIG. 2.

Figure 3:
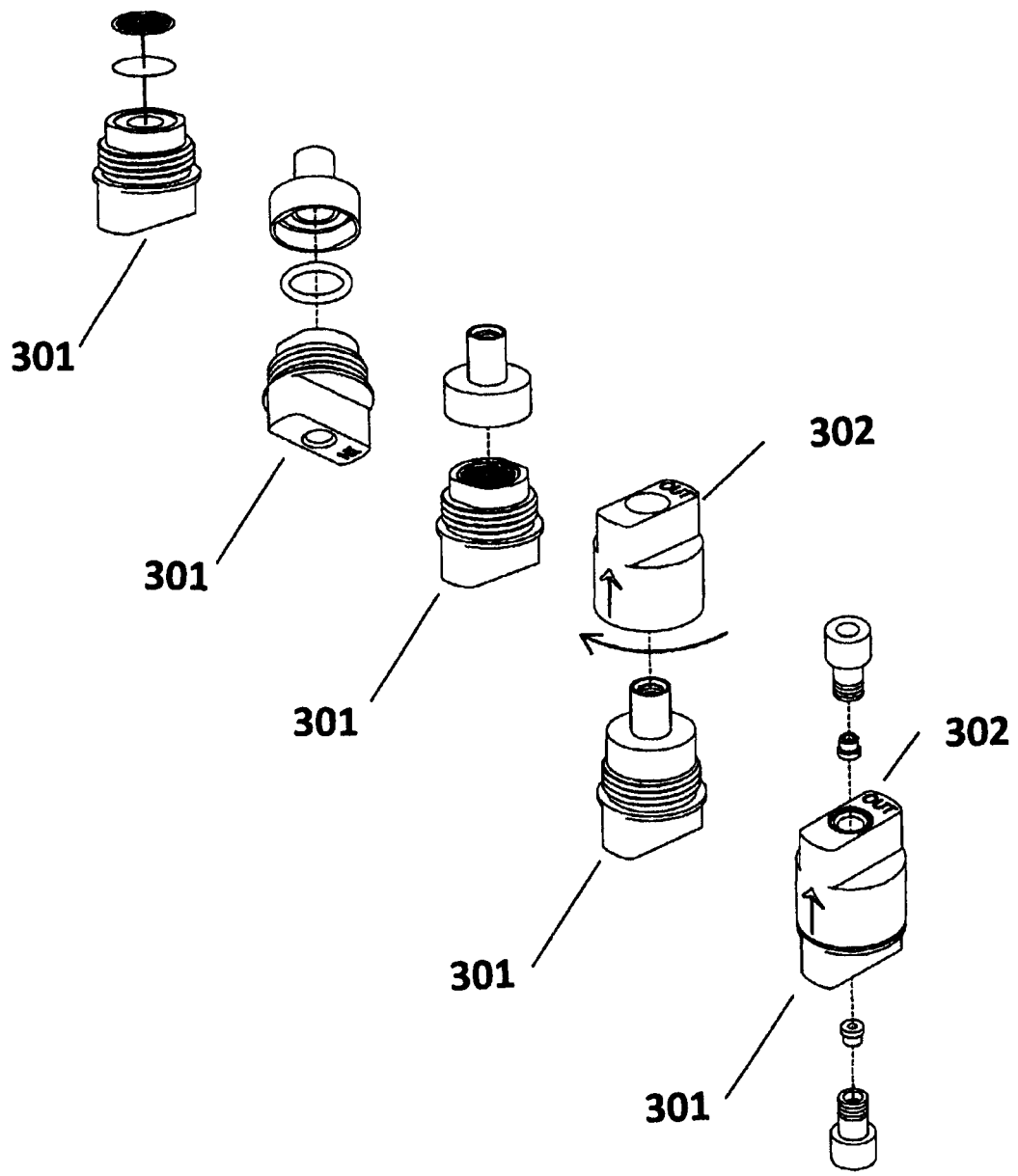
FIG. 3 illustrates a method of assembly for an embodiment of a filter housing assembly for use in the present invention.

FIG. 3 exhibits means by which the low volume filter housing assembly is put together and the elements combined. The filter housing elements 301 and 302 may be screwed together by hand without the need for tools, and the finger tight seal is adequate for even high pressure systems. The same is true when connecting the filter housing assembly to the flowing system by means of finger tight fittings, either cone or flangeless, thus obviating the need for any tools.

Figure 4:
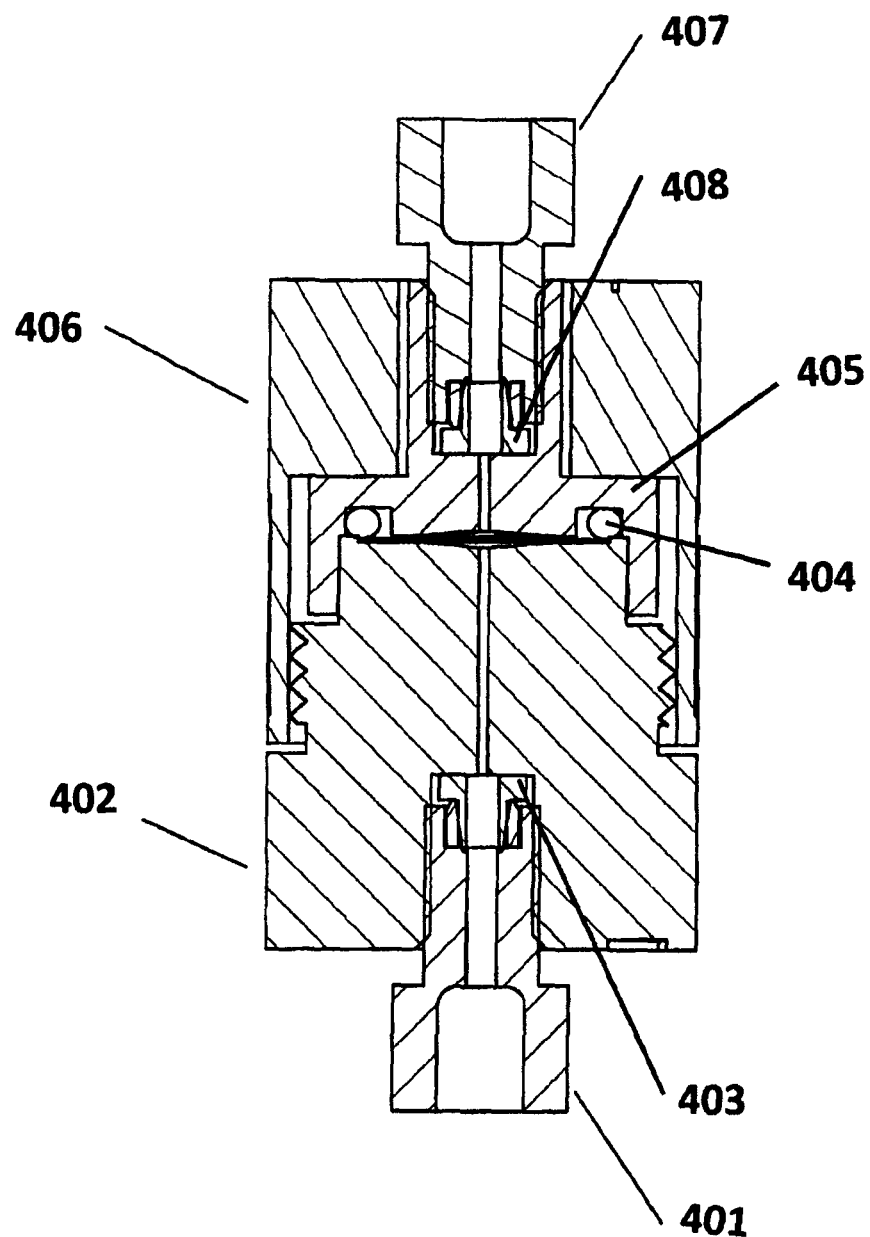
FIG. 4 shows a cross section of an embodiment of a filter housing assembly for use in the present invention when assembled.

A cross section of the assembled low volume filter housing assembly is illustrated in FIG. 4. In the fully assembled low volume filter housing assembly, the inlet fitting 401 is screwed into the inlet filter housing 402. Ferrule element 403 holds the inlet tubing (not shown) in place. The filter element and porous filter element are sealed by the compressed O-ring 404 which is placed between the filter and porous filter elements and the O-ring retainer 405. The O-ring retainer 405 compresses the O-ring 404 by means of downward pressure applied on the O-ring retainer by the outlet filter housing 406 which is screwed onto the inlet filter housing 402. The outlet fitting 407 is threaded into the O-ring retainer 405 and presses upon the outlet ferrule element 408.

Each element of the low volume filter housing assembly may be made of a material suitable for the desired application as discussed above. For example, if aqueous buffers are to be filtered, it may be important that all wetted elements be non-reactive therewith, and thus wetted elements may be made of polyether ether ketone (PEEK), which is an organic polymer thermoplastic commonly used in HPLC systems. Alternatively, some organic solvents are incompatible with PEEK, and therefore wetted elements may be made of, for example, stainless steel. In other embodiments, some elements may be made of one material, and other elements may be made of another material. Also non-wetted elements may be chosen for attributes other than reactivity with solvents and samples, such as ease of manufacture, expense or mechanical durability. For example, the outlet filter housing is generally non-wetted, and therefore it could be made of a very durable material such as stainless steel while the remainder of the elements might be made of PEEK.

One element of the low volume filter of the present invention is the porous filter element 203 as shown in FIG. 2. In one embodiment, this porous filter element is of a woven structure of a suitable metal such as stainless steel and is porous in the central regions of its generally circular shape, but is non-porous at the perimeter, as discussed above. This porous filter element enables a particularly good seal and minimizes potential leakage. However, there are other possible ways to form this porous filter element. For example, the porous filter element might be manufactured in the same way as described above, but fabricated from a different metal such as titanium. Alternatively, it could be made of a combination of materials, such as a stainless steel bound to a PEEK perimeter. In another embodiment, the porous filter element is of a non-woven structure of, for example, PEEK or a carbon composite and is porous in the central regions of its generally circular shape, but can be non-porous at the perimeter, as discussed above. Other possible embodiments do not require that the porous filter element be non-porous along its perimeter, as the O-ring 404 is capable of sealing the system, as shown in FIG. 4, between the O-ring retainer 405 and the inlet filter housing 402.

Figure 5:
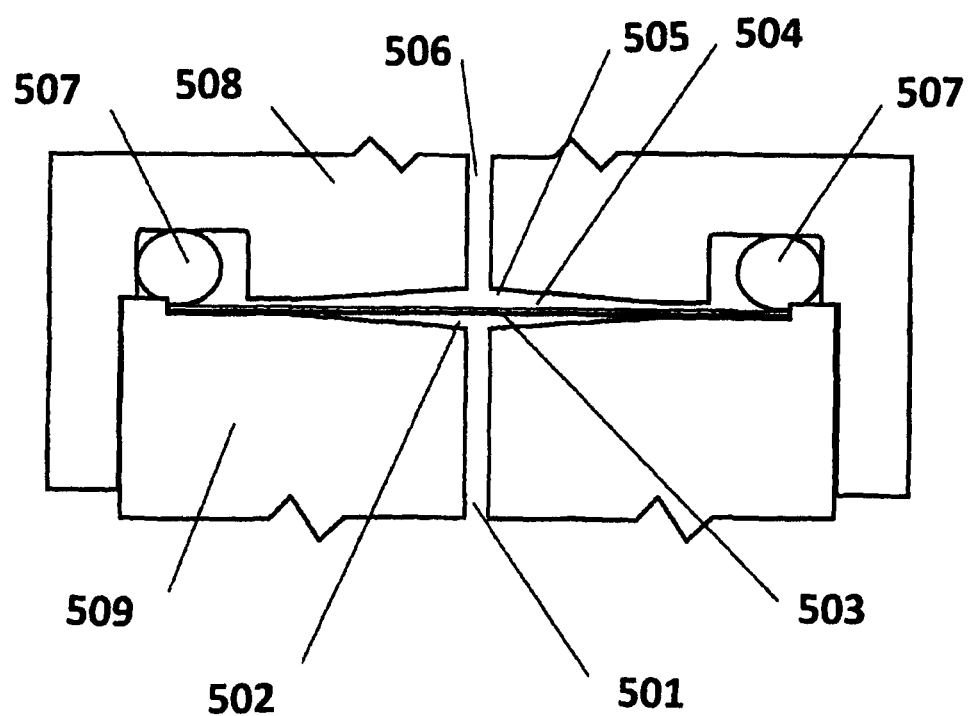
FIG. 5 is a close-up cross section of the flow area near the low volume filter of the assembled invention as shown in FIG. 4.

A close-up cross section of the region surrounding the porous filter element is shown in FIG. 5. Fluid flows through the inlet channel 501 into the inlet 502 until it is of adequate pressure to pass through the porous filter element 503 which is supported by the filter support 504 before filling the outlet 505 and passing into the outlet channel 506. O-ring 507 is compressed such that a seal is maintained between the O-ring retainer 508 and the filter support 504 and the inlet housing 509. The design enables maximal use of the surface area of the filter element due to the positioning and shape of the inlet and outlet 502 and 505.

Figure 6A:
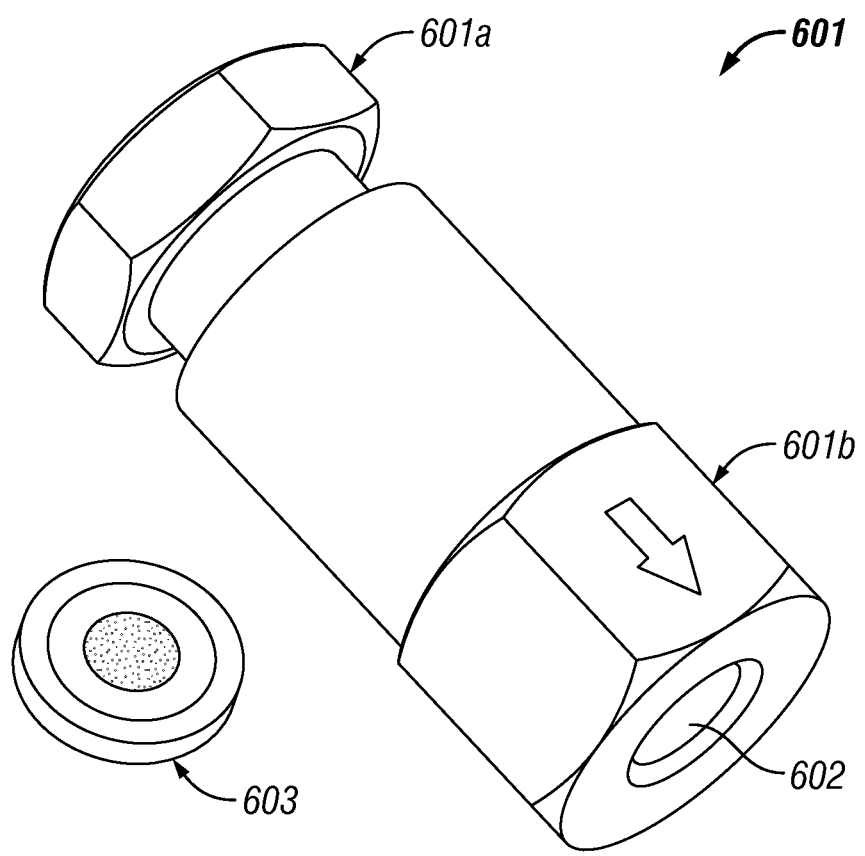
FIG. 6a shows one embodiment of a filter housing assembly for use in the present invention as assembled.
Figure 6B:
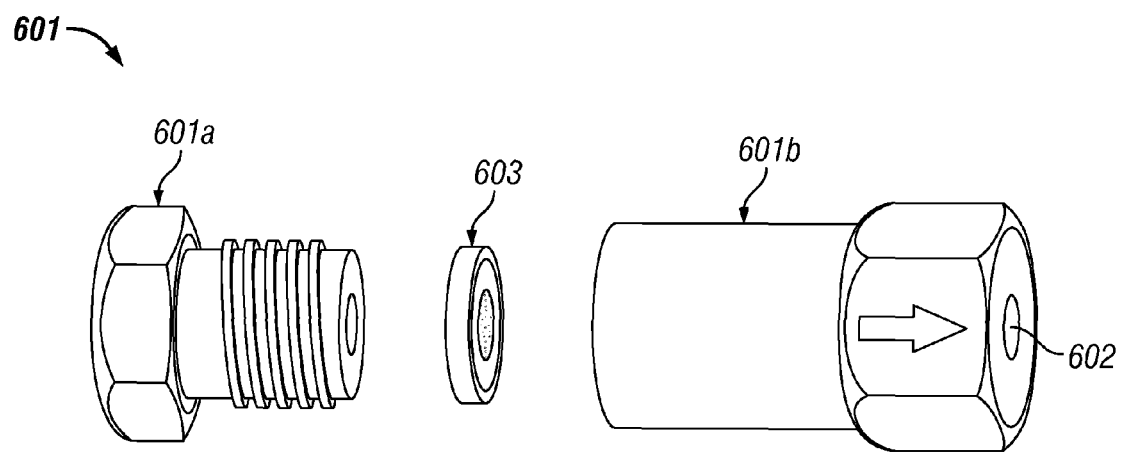

In another embodiment of the present invention, FIG. 6a illustrates a low volume filter 601 for use in the present invention. FIG. 6a shows an inlet filter housing 601a with an opening (not shown) for receiving the flow of the sample to be filtered and an outlet filter housing 601b with opening 602 for flow of the liquid sample, i.e., effluent, of the filtered liquid sample. FIG. 6a also shows porous filter element 603. FIG. 6b shows an exploded view of low volume filter 601 for use in the present invention. In the fully assembled low volume filter, the inlet filter housing 601a can be operatively connected to outlet filter housing 601b by way of, for example, screwing inlet filter housing 601a into outlet filter housing 601b. The opening (not shown) in inlet filter housing 601a will hold an inlet tubing (not shown) in place for receiving the liquid sample to be filtered and opening 602 in outlet filter housing 601b will hold an outlet tubing (not shown). The porous filter element 603 is sealed in the inlet filter housing 601a and outlet filter housing 601b when inlet filter housing 601a is operatively connected to outlet filter housing 601b.

The method of fabrication of the one or more filters for use in the methods of the present invention is within the purview of one skilled in the art and need not be discussed herein.

Step (b) of the method of the present invention involves determining one or more solubility characteristics of the precipitated asphaltenes once substantially all of the alkane soluble fraction has eluted. The one or more solubility characteristics of the precipitated asphaltenes to be determined include, by way of example, solubility parameters, miscibility numbers, Kauri-butanol numbers, dipole moments, relative permitivities, polarity indexes, refractive indexes and specific types of intermolecular interaction in liquid media such as acid and base numbers. Various ways to determine the one or more solubility characteristics of the precipitated asphaltenes are within the purview of one skilled in the art. For example, solubility characteristics of the precipitated asphaltenes can be determined according to the following methods: (1) Solubility Fraction Method; and (2) Solubility Profile Method.

Solubility Fraction Method

The solubility fraction method involves the step of determining one or more solubility characteristics of the precipitated asphaltenes by (1) dissolving at least part of the amount of the precipitated asphaltenes in one or more second solvents having a solubility parameter at least 0.7 $MPa^{0.5}$ higher than the one or more first solvents; and (2) dissolving a second amount of the precipitated asphaltenes in one or more third solvents having a solubility parameter higher than the one or more second solvents, wherein the solubility parameter of the one or more third solvents is at least about 21 $MPa^{0.5}$ but no greater than about 30 $MPa^{0.5}$. A solubility parameter as described herein is determined by the Hansen's methodology described in Barton, A. F. M. *Handbook of Solubility Parameters and Other Cohesion Parameters*; CRC Pres Inc.: Boca Raton, Fla., p. 95 (1983).

Suitable one or more second solvents having a solubility parameter at least 0.7 $MPa^{0.5}$ higher than the one or more first solvents can be determined by one skilled in the art.

Useful solvents include, but are not limited to, one or more alkane solvents, one or more chlorinated hydrocarbon solvents, one or more aromatic solvents, one or more ether solvents, one or more alcohol solvents and the like and mixtures thereof. Representative examples of such solvents can be any of those disclosed above. It is also contemplated that blends of such solvents can be used. In one embodiment, a blend can contain from about 0.5 wt. % to about 99.5 wt. % chlorinated solvent and from about 99.5 wt. % to about 0.5 wt. % alkane solvent. In another embodiment, a blend can contain from about 10 wt. % to about 25 wt. % chlorinated solvent and from about 90 wt. % to about 75 wt. % alkane solvent.

Suitable one or more third solvents having a solubility parameter higher than the one or more second solvents, wherein the solubility parameter of the one or more third solvents is at least about 21 $MPa^{0.5}$ but no greater than about 30 $MPa^{0.5}$, can be determined by one skilled in the art. Generally, the one or more third solvents will dissolve any remaining precipitated asphaltenes captured in the one or more low volume filters. Useful solvents include, but are not limited to, one or more alcohol solvents, one or more chlorinated hydrocarbon solvents, one or more aromatic solvents, one or more ether second solvents and the like and mixtures thereof. Representative examples of such solvents can be any of those disclosed above. It is also contemplated that blends of such solvents can be used. In one embodiment, a blend can contain from about 0.5 wt. % to about 99.5 wt. % chlorinated solvent and from about 99.5 wt. % to about 0.5 wt. % alcohol solvent. In another embodiment, a blend can contain from about 80 wt. % to about 95 wt. % chlorinated solvent and from about 20 wt. % to about 5 wt. % alcohol solvent.

If desired, one or more additional solvents or solvent blends can be used to dissolve at least part of the amount of the precipitated asphaltenes remaining in the one or more low volume filters after the addition of the one or more second solvents and before the addition of the one or more third solvents. In general, the one or more additional solvents or solvent blends will have a solubility parameter greater than the previously added one or more solvents or solvent blends and less than the solubility parameter of the one or more third solvents. For example, one or more fourth solvents having a solubility parameter between the solubility parameter of the one or more second solvents and the solubility parameter of the one or more third solvents can be added to dissolve at least part of the amount of the precipitated asphaltenes. In another embodiment, one or more fifth solvents having a solubility parameter between the solubility parameter of the one or more fourth solvents and the solubility parameter of the one or more third solvents can be added to dissolve at least part of the amount of the precipitated asphaltenes. In yet another embodiment, one or more sixth solvents having a solubility parameter between the solubility parameter of the one or more fifth solvents and the solubility parameter of the one or more third solvents can be added to the dissolve at least part of the amount of the precipitated asphaltenes.

Suitable additional solvents include, but are not limited to, one or more alkane solvents, one or more chlorinated hydrocarbon solvents, one or more alcohol solvents, one or more aromatic solvents and the like and mixtures thereof. Representative examples of such solvents can be any of those disclosed above.

In another embodiment, step (b) of the solubility fraction method includes the steps of (i) dissolving at least part of the amount of the precipitated asphaltenes in one or more second solvents having a dispersion solubility parameter at least about 0.4 $MPa^{0.5}$ higher than the dispersion solubility parameter of the one or more first solvents; and a total solubility parameter at least about 0.7 $MPa^{0.5}$ higher than the one or more first solvents; and (ii) dissolving a second amount of the precipitated asphaltenes in one or more third solvents having a dispersion solubility parameter at least about 1.5 $MPa^{0.5}$ higher than the dispersion solubility parameter of the one or more second solvents; wherein the total solubility parameter of the one or more third solvents is at least about 17.8 $MPa^{0.5}$ but no greater than about 25 $MPa^{0.5}$. Suitable second and third solvents include any of the foregoing second and third solvents.

If desired, prior to step (ii) the following steps can be carried out dissolving at least part of the amount of the precipitated asphaltenes in one or more fourth solvents having a dispersion solubility parameter between at least 0.4 $MPa^{0.5}$ than the dispersion solubility parameter of the second solvent and the solubility parameter of the third solvent; and a total solubility parameter between the total solubility parameter of the second solvent and the total solubility parameter of the third solvent; and dissolving at least part of the amount of the precipitated asphaltenes in one or more fifth solvents having a dispersion solubility parameter at least 0.8 $MPa^{0.5}$ than the dispersion solubility parameter of the second solvent between the solubility parameter of the fourth solvent and the solubility parameter of the third solvent; and a total solubility parameter between the total solubility parameter of the fourth solvent and the total solubility parameter of the third solvent. Suitable fourth and fifth solvents include any of the foregoing fourth and fifth solvents.

The asphaltene concentration in the eluted fractions from the one or more low volume filters is continuously monitored using, for example, a liquid chromatography detector which generates a signal proportional to the amount of each eluted fraction and is recorded in a manner well known in the art. There are a number of commercially available liquid chromatography detectors that can be used including, e.g., refractive index detectors, mass spectrometry, liquid chromatography/mass spectrometry, NMR spectroscopy, Raman spectroscopy, infrared spectroscopy, fluorescence spectroscopy, UV-Vis spectroscopy, diode array detector, Charged Aerosol, evaporative light scattering detectors (ELSD) and the like; all of which can be used in the methods described herein. Other online detectors are known to those skilled in the art. Quantification can then be performed using methods known in the art, e.g., using commercially-available computer programs.

In one preferred embodiment, an evaporative light scattering detector is used as a liquid chromatography detector to monitor each eluting sample's concentration to determine the solubility characteristics of the precipitated asphaltenes. The operating principle of an evaporative light scattering detector is as follows: the compounds to be analyzed are transported by a mobile phase or a more volatile carrier liquid which is then nebulized and evaporated at a relatively low temperature (being able to be in the order of from about 30 to about 150° C.) so that residual micro-particles alone remain—ideally the compounds to be analyzed—which can be detected by light scattering. In this manner, it is possible to analyze directly effluents which originate from the one or more low volume filters under the condition of selecting a mobile phase which is volatile enough to be directly used as a carrier liquid for the evaporative light scattering detector.

For example, in the case of the asphaltenes for the asphaltene fraction method, the result is a single peak for each eluted solvent fraction with each peak representing a solubility characteristic of the asphaltenes.

Solubility Profile Method

The solubility profile method involves the step of determining one or more solubility characteristics of the precipitated asphaltenes by dissolving a first amount and a second amount of the precipitated asphaltenes by gradually and continuously changing the alkane mobile phase solvent to a final mobile phase solvent having a solubility parameter at least 1 MPa$^{0.5}$ higher than the alkane mobile phase solvent. Generally, the first amount of the precipitated asphaltenes (also referred to as "easy to dissolve asphaltenes") will have a lower solubility parameter than the second amount of asphaltenes (also referred to as "hard to dissolve asphaltenes"). The term "gradually" as used herein shall be understood to mean that the alkane mobile phase solvent is incrementally removed from the one or more low volume filters over a period of time by continuously adding a final mobile phase solvent having a solubility parameter at least 1 MPa$^{0.5}$ higher than the alkane mobile phase solvent to the one or more low volume filters. Generally, gradually and continuously changing from essentially the alkane mobile phase solvent to the final mobile phase solvent can occur during a period of about 5 minutes to about 120 minutes at a flow rate of about 0.5 mL/min. to about 4 mL/min. In one embodiment, gradually and continuously changing from the alkane mobile phase solvent to the final mobile phase solvent can occur during a period of about 15 minutes to about 30 minutes at a flow rate of about 0.5 mL/min. to about 4 mL/min.

The first amount of the precipitated asphaltenes are dissolved by gradually and continuously changing the alkane mobile phase solvent to a first final mobile phase solvent having a solubility parameter at least 1 MPa$^{0.5}$ higher than the alkane mobile phase solvent. As one skilled in the art will readily appreciate, the selection of the first final mobile phase solvent will depend on such factors as moving from a low solubility parameter solvent (low solvent power) to a high solubility parameter solvent (high solvent power) using solvents that have the right combination of dispersion, polar and hydrogen bonding forces. For example, a first final mobile phase solvent such as a chlorinated hydrocarbon solvent, e.g., dichloromethane, an ether solvent, an aromatic hydrocarbon solvent or mixtures thereof is gradually and continuously supplied to the one or more low volumefilters to sequentially change the alkane mobile phase solvent from 100% alkane mobile phase solvent to 100% first final mobile phase solvent, i.e., the alkane mobile phase solvent is changed to 1% dichloromethane in 99% alkane mobile phase solvent, then to 2% dichloromethane in 98% alkane mobile phase solvent, until the mobile phase solvent supplied to the one or more low volumefilters is 100% dichloromethane and 0% alkane mobile phase solvent. In this manner, a first amount of the precipitated asphaltenes (i.e., easy to dissolve asphaltenes) will be gradually dissolved and a characteristic elution pattern generated, which is referred to as the asphaltene solubility profile, as discussed hereinbelow.

After the first amount of precipitated asphaltenes has been gradually dissolved, a second or remaining amount of the precipitated asphaltenes (which are not capable of being redissolved in the one or more first final mobile phase solvents) is left in the one or more low volume filters. Thus, in order to redissolve the second amount of precipitated asphaltenes, also referred to as hard to dissolve asphaltenes (i.e., higher solubility parameter asphaltenes), it is may be necessary to supply one or more second final mobile phase solvents having a solubility parameter at least 1 MPa$^{0.5}$ higher than the first final mobile phase solvent to the one or more low volume filters in order to substantially dissolve the remaining amount of the precipitated asphaltenes still captured in the one or more low volume filters and generate a characteristic elution pattern of the hydrocarbon-containing feedstock. This can advantageously allow for a more accurate determination of the solubility profile of the various asphaltene components in the hydrocarbon-containing feedstock.

The selection of the second final mobile phase solvent will depend on such factors as moving from a lower solubility parameter solvent (the first final mobile phase solvent) to a higher solubility parameter solvent (the second final mobile phase solvent) using solvents that have the right combination of dispersion, polar and hydrogen bonding forces. A suitable one or more second final mobile phase solvent can readily be determined by one skilled in the art, e.g., a $C_1$ to $C_6$ alcohol such as methanol. Accordingly, in one embodiment, methanol is gradually and continuously supplied the one or more low volume filters to sequentially change the first final mobile phase solvent, e.g., dichloromethane, from 100% dichloromethane to 100% methanol, i.e., dichloromethane is first changed to 1% methanol in 99% dichloromethane, then to 2% methanol in 98% dichloromethane, until the second final mobile phase solvent supplied to the one or more low volume filters is 100% methanol and 0% dichloromethane.

In another embodiment, step (b) of the solubility profile method includes (i) gradually and continuously changing the one or more first solvents to a first final mobile phase solvent having a dispersion solubility parameter at least about 2.0 MPa$^{0.5}$ higher than the one or more first solvents to dissolve a first amount of the precipitated asphaltenes; and a total solubility parameter at least about 2.0 MPa$^{0.5}$ higher than the one or more first solvents; and (ii) gradually and continuously changing the first final mobile phase solvent to a second final mobile phase solvent having a dispersion solubility parameter at least about 1 MPa$^{0.5}$ higher than the first final mobile phase solvent to dissolve a second amount of the precipitated asphaltenes and a total solubility parameter at least about 1 MPa$^{0.5}$ higher than the first final mobile phase solvent to dissolve a second amount of the precipitated asphaltenes.

The flow rate and time period for gradually and continuously supplying the one or more second final mobile phase solvents are substantially the same as for the first final mobile phase solvents.

The asphaltene concentration in the eluted fractions from the one or more low volume filters is continuously monitored using, for example, a liquid chromatography detector as discussed hereinabove. In one preferred embodiment, an evaporative light scattering detector is used as a liquid chromatography detector to monitor each eluting sample's concentration. The operating principle of an evaporative light scattering detector is as follows: the compounds to be analyzed are transported by a mobile phase or a more volatile carrier liquid which is then nebulized and evaporated at a relatively low temperature (being able to be in the order of from about 30 to about 150° C.) so that residual micro-particles alone remain—ideally the compounds to be analyzed—which can be detected by light scattering. In this manner, it is possible to analyze directly effluents which originate from the one or more low volume filters under the condition of selecting a mobile phase which is volatile enough to be directly used as a carrier liquid for the evaporative light scattering detector. For example, in the case of the asphaltenes, the result is a curve that represents the solubility parameter distribution of the asphaltenes.

Next, a solubility profile of the asphaltenes in the liquid sample can be created by techniques known in the art. For example, when asphaltenes are quantified using an evaporative light scattering detector, the result is a curve that represents the solubility parameter distribution of the asphaltene in the hydrocarbon-containing feedstock. Since the solubility parameter of a mixture of solvents is given by the volumetric average of the components, it is possible to convert the time scale of the elution to a solubility parameter scale using the following equation:

$$\delta = \sum_{i=1}^{n} \phi_i \delta_i$$

wherein $\delta$ is the solubility profile of the mixture, $\phi_i$ is the volume fraction and $\delta_i$ is the solubility parameter of each of the components, respectively. The volume fraction is the volume fraction of the blend of each solvent and readily determined by the chromatography apparatus. The solubility parameter of a component is either known in the art, e.g., Barton, A. F. M. *Handbook of Solubility Parameters and Other Cohesion Parameters*; CRC Pres Inc.: Boca Raton, Fla., 1983, or can be determined by techniques within the purview of one skilled in the art.

Step (c) of the method of the present invention involves analyzing the one or more solubility characteristics of the precipitated asphaltenes. For example, by analyzing the one or more solubility characteristics of the precipitated asphaltenes, the asphaltene content or asphaltene stability of the hydrocarbon-containing feedstock sample can be determined.

Determining Asphaltene Content

Once the one or more solubility characteristics have been analyzed for a given hydrocarbon-containing feedstock sample, the asphaltene content can be determined as follows.

Solubility Fraction Method

In the solubility fraction method, the result is one peak for each eluted solvent fraction with each peak representing a solubility characteristic of the asphaltenes. The area under the separate peaks can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Then, each area is correlated to an asphaltene mass according to a calibration curve that depends on the type of detector used as within the purview of one skilled in the art. The calibration may or may not be the same for all the peaks. The total asphaltene mass (TAM) for the sample would therefore be the addition of all the asphaltene masses (M) determined for each peak:

$$TAM = \sum_{i=1}^{n} M_i$$

Solubility Profile Method

In the solubility profile method, the amount of asphaltenes is determined by calculating the area of the second peak of the solubility profile. An asphaltene solubility profile normally shows either two peaks or one peak and one shoulder from the evaporative light scattering detector. The two peaks or peak/shoulder can be separated by numerical methods well known in the art such as, for example, peak deconvolution or peak fitting. The area under the peaks, e.g., the second peak, can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Then, this area is correlated to an asphaltene mass according to a calibration curve. A calibration procedure was developed that relates the measured peak area (A) to the total asphaltene mass in the sample (TAM). The following equation is an example of such correlation that allows the calculation of the asphaltene mass:

Log TAM=0.5336 log $A$−6.097 where TAM is the total asphaltene mass in the sample and A is the area of the second deconvoluted peak respectively.

Determining Asphaltene Stability

In one embodiment, asphaltene stability can be determined from the solubility characteristics of the asphaltenes in the hydrocarbon-containing feedstock sample from the solubility fraction method discussed above. The asphaltene fraction method normally shows a single peak for each eluted solvent fraction from the evaporative light scattering detector which represents the solubility characteristics of the asphaltenes. In one embodiment, the asphaltene stability can be determined from a ratio of the area under the single peaks for each eluted solvent fraction, i.e., once the peaks are known, the areas for each of the peaks are calculated and a ratio between the areas determined. The area under the peaks can be calculated using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). Accordingly, one such way to calculate the ratio is as follows:

Ratio=(area peak 3+area peak 4)/(area peak 1+area peak 2)

wherein peak 1 is the first peak characterizing the first asphaltene fraction eluted from the one or more low volume filters (i.e., easy to dissolve asphaltenes); peak 2 is the second peak characterizing the second asphaltene fraction eluted from the one or more low volume filters; peak 3 is the third peak characterizing the third asphaltene fraction eluted from the one or more low volume filters and peak 4 is the fourth peak characterizing the fourth asphaltene fraction eluted from the one or more low volume filters. In this ratio, the first two peaks (peak 1 and 2) represent "easy to dissolve asphaltenes" that help in the solubilization of the rest of asphaltenes (last two peaks: 3 and 4) also known as "difficult to dissolve asphaltenes". The larger the ratio, the lower the stability since there are less easy to dissolve asphaltenes that help in the solubilization of the difficult to dissolve asphaltenes.

In another embodiment, asphaltene stability can be determined from the solubility profile of the asphaltenes in the hydrocarbon-containing feedstock sample created by the solubility profile method discussed above. For example, asphaltene stability can be mathematically calculated based on the solubility profile of the asphaltenes. An asphaltene solubility profile normally shows either two peaks or one peak and one shoulder from the evaporative light scattering detector. The two peaks or peak/shoulder can be separated by numerical methods well known in the art such as, for example, peak deconvolution or peak fitting. The first resolved peak is generally known as an "easy to dissolve asphaltene" peak and is derived from step (i) which gradually and continuously changes the one or more first solvents to a first final mobile phase solvent having a solubility parameter at least about 1 $MPa^{0.5}$ higher than the one or more first solvents to dissolve a first amount of the precipitated asphaltenes. The second resolved peak or shoulder is generally known as a "hard to dissolve asphaltene" peak and is derived from step (ii) which gradually and continuously changes the first final mobile phase solvent to a second final mobile phase solvent having a solubility parameter at least about 1 $MPa^{0.5}$ higher than the first final mobile phase solvent to dissolve a second, or remaining amount of precipitated asphaltenes.

Examples of calculations to determine asphaltene stability include the following.

1. Average solubility parameter of the hard to dissolve asphaltenes (SPA).

This is a measurement of how difficult it is to dissolve the material eluted in the second peak or shoulder of the solubility profile (i.e., the hard to dissolve asphaltenes). It is calculated as the mean of the distribution corresponding to the second peak or shoulder obtained by the solubility parameter scale calculation discussed above. The higher the value, the more difficult it is to dissolve the hard to dissolve asphaltenes thereby indicating lower stability.

2. Ratio of hard-to-dissolve asphaltenes/easy to dissolve asphaltenes (i.e., second peak area/first peak area ratio wherein the second peak area and first peak area are derived from the solubility profile). After the separation of the peaks discussed hereinabove with respect to the asphaltene solubility profile, the areas for both peaks are calculated and the ratio between both areas determined. The area under the peaks can be determined using commercially available software packages for qualitative and quantitative analysis that include quantification of peak area and height. Commercially available software packages include, by way of example, GRAMS/AI package provided by Thermo Galactic (Salem, N.H.) and Chemstation® by Agilent Technologies (Santa Clara, Calif.). This ratio indicates whether there is enough transitional material or easy to dissolve asphaltenes (first peak) to keep the hard to dissolve (i.e., highly insoluble) asphaltenes (second peak) in solution. Accordingly, a larger ratio indicates a lower amount of transitional material or easy to dissolve asphaltenes present in the hydrocarbon-containing material in comparison with the more polar asphaltenes and hence a higher tendency of the latter to precipitate.

3. Overlapping of hard-to-dissolve asphaltenes to the easy to dissolve asphaltenes. This is a measurement of the compatibility between both species and, therefore, can be used to evaluate stability. After the separation of the peaks discussed hereinabove with respect to the asphaltene solubility profile, the area of both peaks are calculated as well as the overlapping area which corresponds with the area that both peaks share and lie in the same region. Accordingly, a higher value indicates greater stability and, therefore, the asphaltenes are less prone to precipitate.

4. ΔPS measures the broadness of the solubility profile and it is also related to the stability of the asphaltenes in the hydrocarbon-containing feedstock. This parameter is calculated according to the following equation:

$$\Delta PS = t(75\%) - t(25\%)$$

wherein t(75%) and t(25%) represent the time at which 75% and 25% of the asphaltenes in the hydrocarbon-containing feedstock (in terms of area) have eluted, respectively. The ΔPS is calculated based on the cumulative areas of the whole distribution of times or solubility parameters that represent the solubility profile of the asphaltenes in the sample. Accordingly, a higher value indicates that a higher solubility parameter solvent is required to redissolved them and hence they present a lower stability and are more prone to precipitate.

In one embodiment of the present invention, the precipitated asphaltenes are captured in the one or more low volume filters heated to an elevated temperature, e.g., a temperature up to about 350° C. such as a temperature ranging from about 18° C. to about 350° C. After the precipitated asphaltenes are captured in the heated one or more low volume filters, the filter(s) are then cooled to room temperature prior to step (b), and wherein step (b) comprises dissolving at least part of the amount of the precipitated asphaltenes in one or more second solvents having a solubility parameter at least about 0.7 $MPa^{0.5}$ higher than the one or more first solvents as discussed above.

Next, step (c) comprises nebulizing the eluted fraction sample thereby forming a multitude of droplets, the droplets comprising solvent, asphaltene particles and non-asphaltene particles; evaporating the solvent from at least a portion of the multitude of droplets to thereby form a multitude of aerosol particles, wherein the aerosol particles comprise at least a portion of the asphaltene particles and non-asphaltene particles; charging at least a portion of the non-asphaltene particles; and passing the charged non-asphaltene particles through a charge-responsive device disposed to receive the charged non-asphaltene particles and determine the charge.

Generally, a charge-responsive device can be, for example, an electrometer, is a charged aerosol detector (CAD) which is used as a liquid chromatography detector to monitor each eluting sample's concentration to determine the solubility characteristics of the precipitated asphaltenes. A suitable CAD can be any CAD commercially available from such sources as Thermo Scientific (Waltham, Mass.), e.g., Dionex Corona™, ultra RS™ Charged Aerosol Detector. The operating principle of a charged aerosol detector is as follows: The sample is nebulized into droplets, which are subsequently dried into particles. The particle size increases with the amount of sample. A stream of positively charged gas collides with the sample particles. The charge is then transferred to the particles. These particles are transferred to a collector where the charge is measured by a highly sensitive electrometer. This generates a signal in direct proportion to the quantity of sample present. For example, in the case of the asphaltenes, the result is a single peak for the eluted solvent fraction. The area under the asphaltene peak is then measured using conventional high pressure liquid chromatography (HPLC) software packages, Chemstation® by Agilent Technologies (Santa Clara, Calif.), and this area is directly proportional to the asphaltene concentration. For example, the Chemstation software program determines a response factor relating peak area intensity to the amount of grams for each calibrated asphaltene. The software then determines the number of grams of the calibrated asphaltene from the response factor and the peak area.

The following non-limiting examples are illustrative of the present invention.

EXAMPLE 1

Peak Comparison between on-column and in-line filtration devices.

A solution of asphaltenes (extracted from Venezuelan crude oil using ASTM D6560) was prepared by dissolving 0.0100 g of the material in 10 mL of methylene chloride. The solution was tested using two different setups:

Setup A. This setup consisted of a HPLC system composed of a HP Series 1100 chromatograph and an Alltech ELSD 2000 detector using a 10 mm i.d×100 mm stain steel column. The packing material of the column was polytetrafluoroethylene-packed (PTFE) 40-60 mesh.

Setup B. This setup consisted of the same as setup A except that the column was replaced with a low volume filter containing a 0.5 micron stainless steel porous filter element purchased from Restek (cat. No. 24993), having a volume of 5 µL volume (see as http://www.restek.com/catalog/view/10607 as retrieved on Jun. 18, 2014), For both setups A and B, 4 microliters of the solution was injected into each system using a heptane mobile phase at a flow rate of 4 mL/min. The maltenes (heptane solubles) first eluted from the column or filter. Next, the precipitated asphaltenes captured in the column (setup A) or in the filter (setup B) were eluted as follows: after 8 min of the injection of the sample, the mobile phase was switched to a blend a 90/10 methylene chloride/methanol blend at a flow rate of 4 mL/min and after 12 min was switched back to 100% heptane at a flow rate of 4 mL/min.

In setup A, asphaltenes started to elute around 9.10 min. In setup B, asphaltenes started to elute around 8.25 min. In both cases, the eluted asphaltenes were quantified using an Evaporative Light Scattering Detector (ELSD) (Alltech ELSD 2000), which was equipped with a light-scattering photometer, by evaporating the solvent and passing the stream containing non-volatile particles (asphaltenes or maltenes) through the light-scattering photometer. The ELSD operated at the following conditions: drift tube temperature 75° C.; volumetric flow of the solvents was 4 mL/min. and 3.5 L/min. of nitrogen as the nebulizing gas. The light scattered by the non-volatile particles was collected and it was a measure of the concentration of the solute in the effluent.

Figure 7:
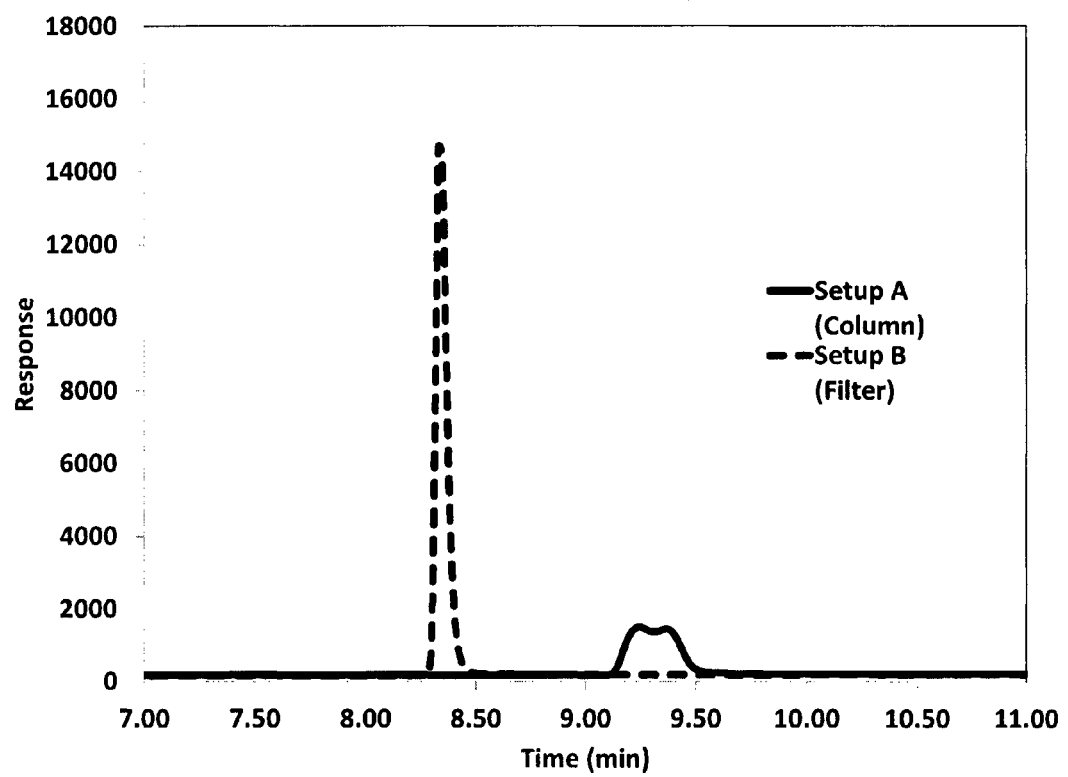
FIG. 7 shows the response for the eluted asphaltenes obtained using setups A and B of Example 1.

FIG. 7 shows the response for the eluted asphaltenes obtained using the different setups. This figure indicates that the filter device provides a narrower peak indicating better resolution. The main contributing factor to the broadness of the peaks when setup A was used was the high volume of the column (3.4 mL) in comparison with the low volume of the filter (5 µL). In addition, it is clear that the signal-to-noise ratio would be significantly larger for the peak obtained using the column thereby decreasing the limit of quantification. Finally, the appearance of two unresolved peaks on the signal obtained using the column in setup A indicates that there is a certain degree of interaction or adsorption with the substrate going on, which is absent in the low volume filter, and it should be avoided if asphaltenes will be separated by its solubility in different solvents.

EXAMPLE 2

Calibration Curves

A solution of asphaltenes (extracted from Venezuelan crude oil using ASTM D6560) was prepared by dissolving 0.0100 g of the asphaltenes in 10 mL of methylene chloride. Different volumes of solution (i.e., 1 microliter, 2 microliter, 5 microliters, and 8 microliters) were passed through the low volume filter described in Example 1 using a heptane mobile phase at a flow rate of 2 mL/min. The maltenes (heptane solubles) first eluted from the column or filter. Next, the precipitated asphaltenes captured in the filter were eluted as follows: after 2 min of the injection of the sample, the mobile phase was switched to 90/10 methylene chloride/methanol blend and after 4 min was switched back to 100% heptane. The asphaltenes were quantified using an ELSD equipped with a light-scattering photometer as in Example 1. The area A corresponding to the asphaltenes signal was determined for each injection volume and related to the asphaltene masses M according to:

$$\log M = B \log A + C \qquad (1)$$

where B and C are the calibration constants.

Figure 8:
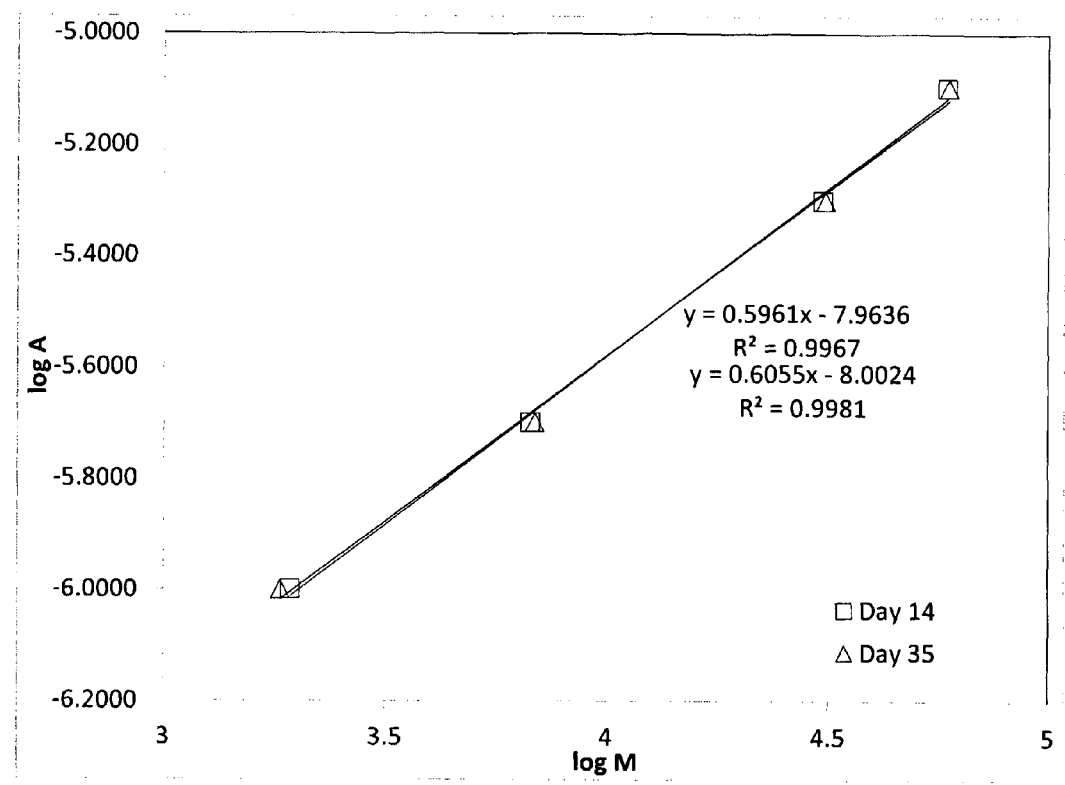
FIG. 8 shows a set of two calibration curves obtained for the same filter in different days of Example 2.

Regression analysis was used to calculate the calibration constants. FIG. 8 shows a set of two calibration curves obtained for the same filter in different days.

As it can be seen, the results show a relatively good agreement between the different calibration curves. Additionally, excellent correlation coefficients were obtained. For day 14, the calibration equation is:

$$\log M = 0.5961 \log A - 7.9636 \quad r^2 = 0.9967$$

For day 35, the calibration equation is:

$$\log M = 0.6055 \log A - 8.0024 \quad r^2 = 0.9981$$

EXAMPLE 3

Repeatability Comparison between on-column and in-line filtration devices.

Solutions of a crude oil from Venezuela (0.1000 g in 10 mL of methylene chloride) were repeatedly (20 times) prepared and tested for asphaltene content during a month using the setups A and B of Example 1.

Four microliters of solution were injected into the system using a heptane mobile phase at a flow rate of 4 mL/min. The maltenes (heptane solubles) first eluted from the column or filter. Next, the precipitated asphaltenes captured in the column (setup A) or in the filter (setup B) were eluted as follows: after 8 min of the injection of the sample, the mobile phase was switched to 90/10 methylene chloride/methanol blend at a flow rate of 4 mL/min and after 12 min, was switched back to 100% heptane at a flow rate of 4 mL/min.

For Setup B the procedure was similar to Setup A, except that a flow rate of 2 mL/min was used to save solvent. For Setup A, a flow rate of 2 mL/min will decrease considerable the quality of the peak (it will make them wider and closer to the baseline).

Figure 9:
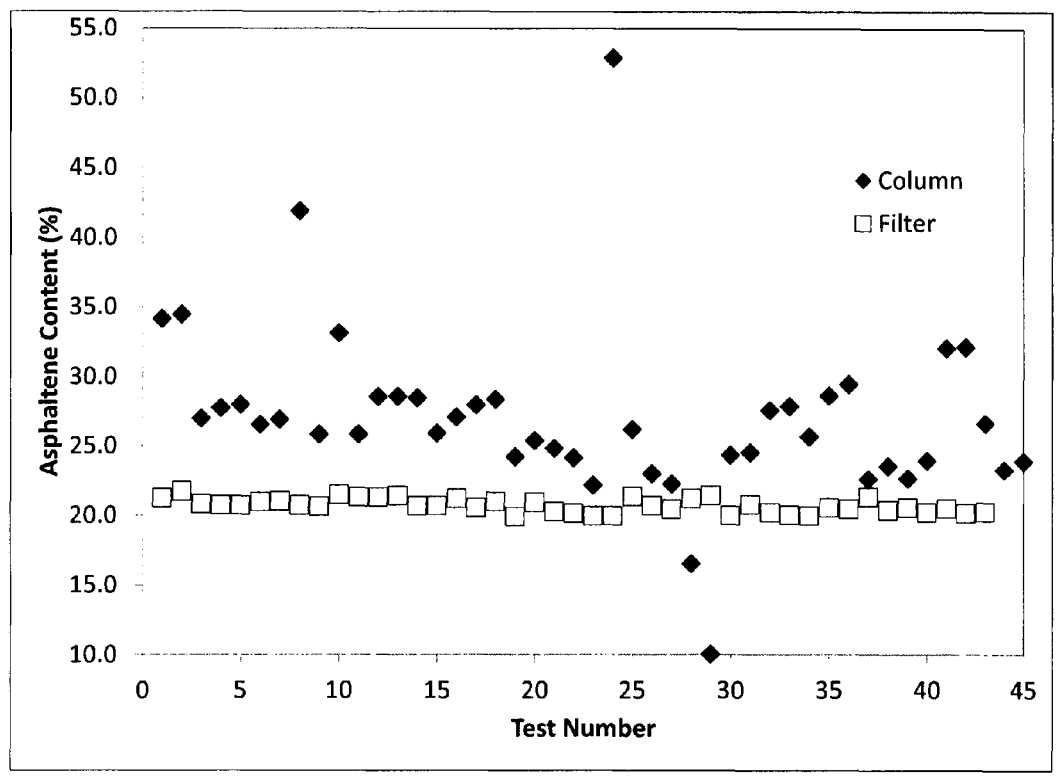
FIG. 9 shows the repeatability comparison between on-column and in-filtration devices of Example 3.

Asphaltene quantification was carried out using the ELSD as in Example 1. Repeatabilities are shown in FIG. 9. Average values and standard deviations are 27.2±5.9 and 20.7±0.5 for setups A and B respectively. These values clearly show that the use of the filter increases the repeatability of the measurements. It is also noticeable that the values obtained using the column are larger indicating as in Example 1 that there might be adsorption of material on the column.

EXAMPLE 4

Repeatability when replacing filters and columns.

Solutions of a crude oil from Venezuela (0.1000 g in 10 mL of methylene chloride) were repeatedly (6 times) prepared and tested for asphaltene content several times (2 times each one) using the setups A and B of Example 1, except that the filters and columns used in Example 3 were replaced. The low volume filter was replaced with the same commercially available low volume filter. The columns were manually filled in the laboratory following the "tap-fill" method (according to the following reference: Snyder, et al., "Introduction to Modern Liquid Chromatography." 1997. Wiley, pp 207.) for dry packing of rigid solids. For this example, 2 low volume filters and 3 columns were tested. The experiments were carried out in substantially the same manner as in Example 3: 4 mL/min was used for setup A, and 2 mL/min was used for setup B.

Figure 10:
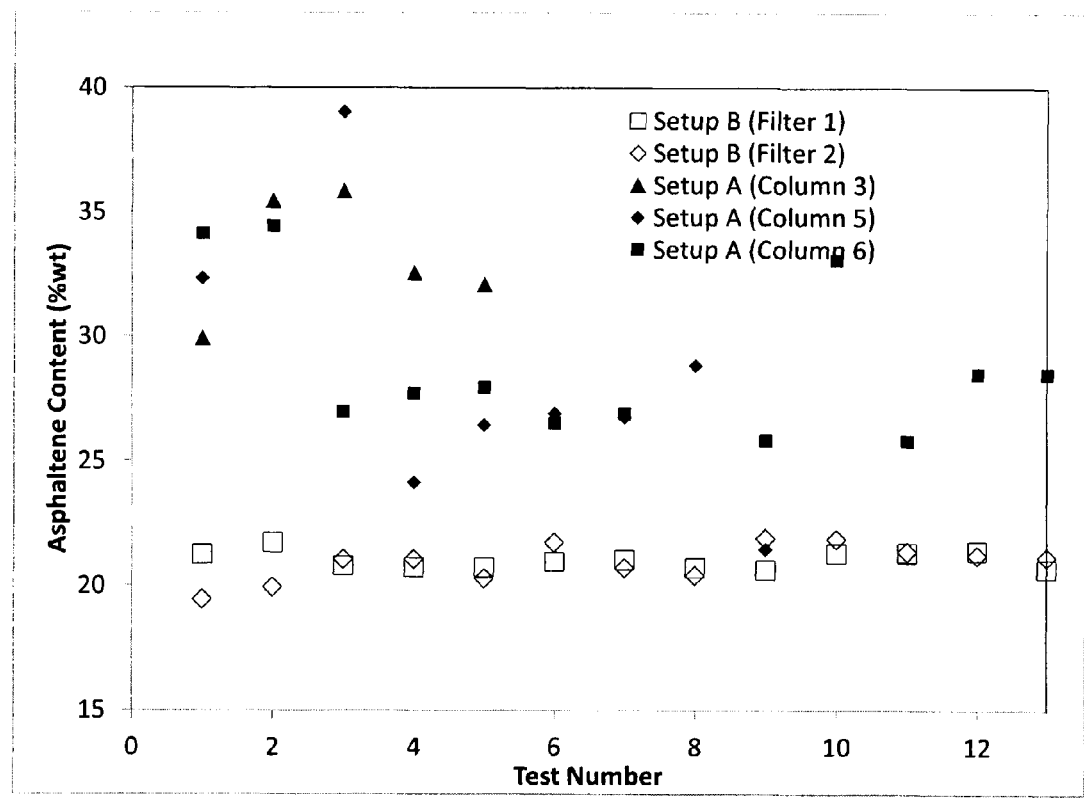
FIG. 10 shows the repeatability when replacing filters and columns of Example 4.

FIG. 10 shows the repeatability of both groups of experiments. Both low volume filters 1 and 2 were very similar in performance (20.9% and 21.0% in average values with a standard deviation of 0.6). The columns showed a much higher variability (33.2%, 29.8% and 30.3% in average values with a standard deviation of 5.0).

EXAMPLE 5

Comparison of asphaltene content determination by filtration and asphaltene content determination using ASTM D6560.

Figure 11:
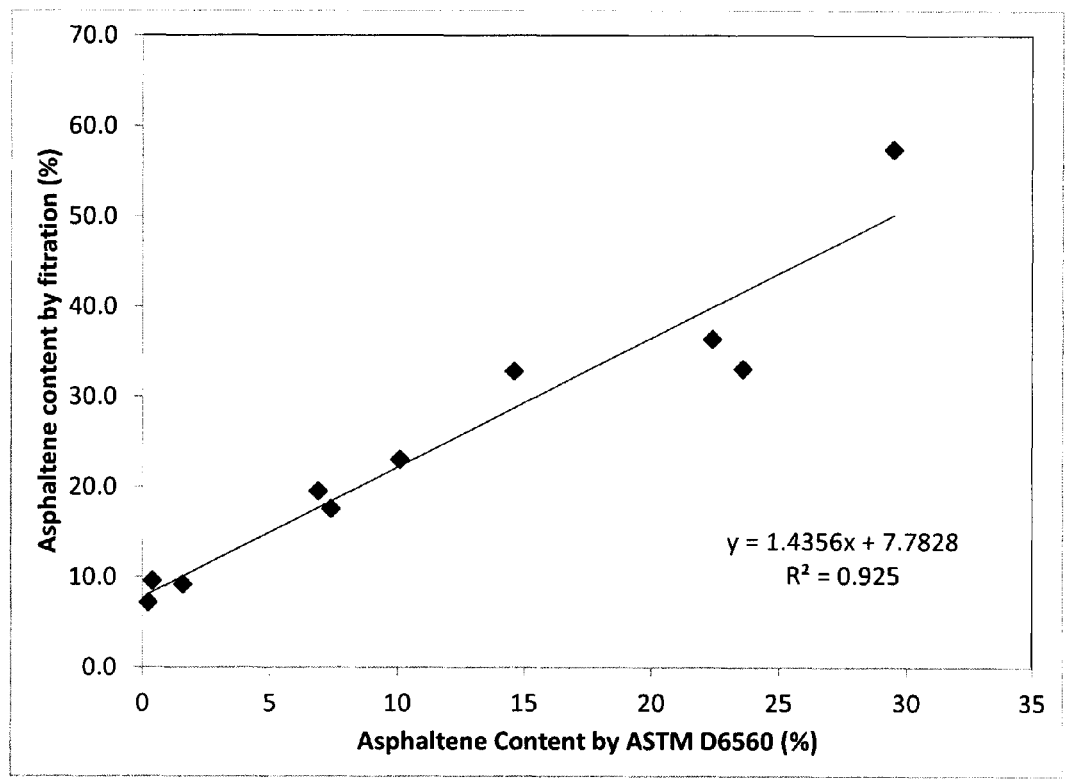
FIG. 11 shows the comparison of both sets of values of asphaltene content determination by filtration and asphaltene content determination using ASTM D6560 of Example 5.

Solutions of 10 different hydrocarbon-containing materials were prepared by dissolving 0.1000 g of the material in 10 mL of methylene chloride. All of the solutions were injected using setup B of Example 1 and following the procedure described in Example 2. Similarly, the same samples were tested according to standard test ASTM D6560. FIG. 11 shows the comparison of both sets of values of asphaltene content determination by filtration and asphaltene content determination using ASTM D6560. The plot indicates that both set of results are similar. The results obtained by the filtration test were larger than those using ASTM D6560. However, ASTM 6560 is performed at 80° C., while the filtration test is done at room temperature.

EXAMPLE 6

Comparison of performance at low asphaltene concentrations between on-column and in-line filtration devices.

A solution of a heavy Venezuelan crude oil (0.1000 g in 10 mL of dichloromethane) was prepared and its asphaltene content was determined using setups A and B of Example 1 and following the procedure described in Example 3. Next, toluene solutions of the crude oil were prepared ranging from 30 ppm to 2500 ppm. 4 microliters of the toluene solutions containing from 30 ppm to 2500 ppm of the heavy Venezuelan crude oil were injected directly in setups A and B according to the procedures mentioned in Examples 3 and 4. The results obtained were compared with the values obtained based on the solution of a heavy Venezuelan crude oil (0.1000 g in 10 mL of dichloromethane).

Figure 12:
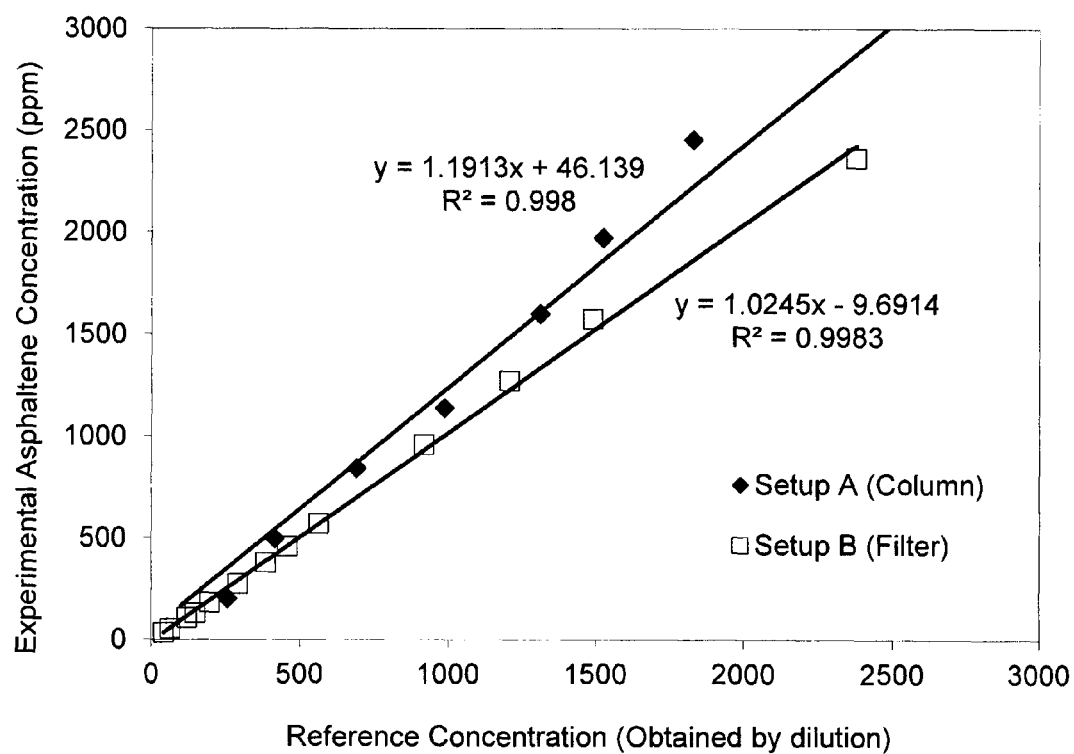
FIG. 12 shows the comparison between the results obtained using the two different setups A and B of Example 6 and the expected real or reference values calculated by dilution.

FIG. 12 shows the comparison between the results obtained using the two different setups A and B and the expected real or reference values calculated by dilution. According to the fitting of the data the on-column method overestimated the amount of asphaltene by about 19%, while the in-line filtration device overestimated by about 2.5%. Additionally, the limit of quantification for both techniques was found to be: 250 ppm and 30 ppm for setup A and B, respectively.

EXAMPLE 7

Comparison of solubility asphaltene fractionation between on-column and in-line filtration devices.

Solutions of 6 different hydrocarbon-containing materials were prepared by dissolving 0.1000 g of the material in 10 mL of methylene chloride. Then, the solutions were injected into setups A and B according to the following procedures:

Setup A.

The flow rate during the whole process was 4 mL/min. 40 microliters of solution were injected using a heptane mobile phase. After 10 min, the asphaltenes remained precipitated in the column and were fractionated according to their respective solubilities by switching the mobile phase in successive steps to solvents of increasing solubility parameters: (1) 10 minutes after the injection of the sample, the mobile phase was switched to a blend of 15% methylene chloride/85% n-heptane (Total Solubility Parameter of 16.1 $MPa^{0.5}$, Dispersion component: 15.8 $MPa^{0.5}$), (2) 20 minutes after the injection of the sample, the mobile phase was switched to a blend of 30% methylene chloride/70% n-heptane (Solubility Parameter of 18.8 $MPa^{0.5}$, Dispersion component: 16.2 $MPa^{0.5}$), (3) 30 minutes after the mobile phase was switched to 100% methylene chloride (Solubility Parameter of 20.3 $MPa^{0.5}$, Dispersion component: 18.2 $MPa^{0.5}$); and (4) 40 minutes after the injection of the sample, the mobile phase was switched to a blend of 10% methanol/90% methylene chloride (Solubility Parameter of 21.2 $MPa^{0.5}$, Dispersion component: 17.9 $MPa^{0.5}$). After 10 additional minutes, the solvent was switched again to n-heptane to prepare the column for the next sample. Four asphaltene fractions were obtained: (1) asphaltenes soluble in 85/15 heptane/methylene chloride (peak 1), (2) 70/30 heptane/methylene chloride (peak 2), (3) 100% methylene chloride (peak 3) and (4) 90/10 methylene chloride/methanol (peak 4). In this manner, four different asphaltenes solubility fractions were separated with a total analysis time of approximately 60 minutes.

Setup B.

The flow rate during the whole process was 2 mL/min. 40 microliters of solution were injected using a heptane mobile phase (Solubility Parameter of 15.3 $MPa^{0.5}$, Dispersion component: 15.3 $MPa^{0.5}$). After 4 min, the asphaltenes remained retained in the filter and were fractionated according to their respective solubilities by switching the mobile phase in successive steps to solvents of increasing solubility parameters: (1) 4 minutes after the injection of the sample, the mobile phase was switched to a blend of 15% methylene chloride/85% n-heptane (Solubility Parameter of 16.1 $MPa^{0.5}$, Dispersion component: 15.8 $MPa^{0.5}$), (2) 8 minutes after the injection of the sample, the mobile phase was switched to a blend of 30% methylene chloride/70% n-heptane (Solubility Parameter of 18.8 $MPa^{0.5}$, Dispersion component: 16.2 $MPa^{0.5}$), (3) 12 minutes after the mobile phase was switched to 100% methylene chloride (Solubility Parameter of 20.3 $MPa^{0.5}$, Dispersion component: 18.2 $MPa^{0.5}$), and (4) 16 minutes after the injection of the sample, the mobile phase was switched to a blend of 10% methanol/90% methylene chloride (Solubility Parameter of 21.2 $MPa^{0.5}$, Dispersion component: 17.9 $MPa^{0.5}$). After 4 additional minutes, the solvent was switched again to n-heptane to prepare the column for the next sample. Four asphaltene fractions were obtained: (1) asphaltenes soluble in 85/15 heptane/methylene chloride (peak 1), (2) 70/30 heptane/methylene chloride (peak 2), (3) 100% methylene chloride (peak 3) and (4) 90/10 methylene chloride/methanol (peak 4). In this manner, four different asphaltenes solubility fractions were separated with a total analysis time of approximately 25 minutes.

The asphaltene stability, i.e., R values, was calculated according to the following equation (2) for both sets:

$$R=(\text{Area peak 3}+\text{Area peak 4})/(\text{Area peak 1}+\text{Area peak 2}) \quad (2)$$

Figure 13:
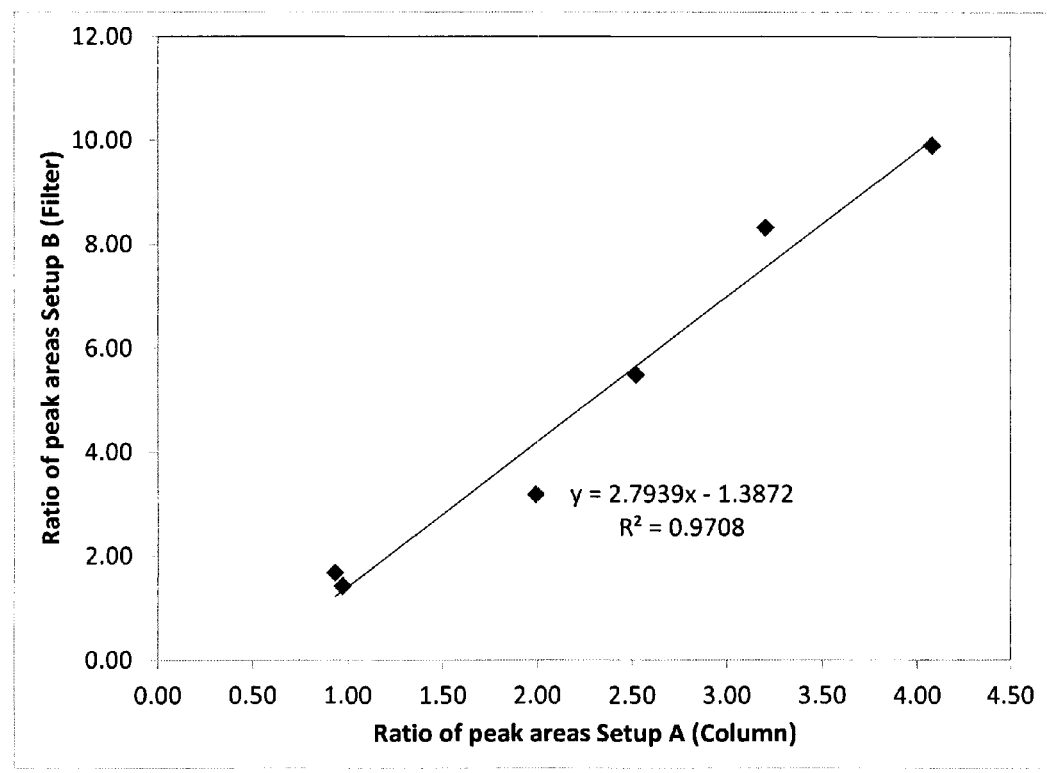
FIG. 13 shows a comparison between the values obtained using setups A and B of Example 7.

FIG. 13 shows a comparison between the values obtained using both setups. This plot demonstrates a good correlation between both sets of results indicating that the in-line filtration method can be applied also to the evaluation of the solubility fractionation of asphaltenes.

EXAMPLE 8

Solubility profile distribution using the in-line filtration device.

Solutions of two hydrocarbon materials (Virgin crude oil and a hydroprocessed product) were prepared by dissolving 0.1000 g of the material in 10 mL of methylene chloride. 40 microliters of both solutions were injected into Setup B from example 7 using a heptane mobile phase (Solubility Parameter of 15.3 MPa$^{0.5}$, Dispersion component: 15.3 MPa$^{0.5}$) at a flow rate of 2 mL/min. Maltenes (heptane solubles) elute from the column at the first peak around 2 min after the injection. After 5 min, the mobile phase was then gradually switched to 90/10 methylene chloride/methanol blend (Solubility Parameter of 21.2 MPa$^{0.5}$, Dispersion component: 17.9 MPa$^{0.5}$) at a flow rate of 2 mL/min and after 10 min, was switched also gradually to 100% methanol at a flow rate of 2 mL/min. The change of the solvent from heptane to the methylene chloride/methanol blend redissolved the asphaltenes and they started to elute around 5.85 min. The gradual change in the solvent from methylene chloride/methanol blend to the methanol redissolved the asphaltenes gradually from the easy to dissolve (lower times) to the hard to dissolve (larger times). The total procedure took 21 min.

Asphaltenes were quantified using an ELSD by evaporating the solvent and passing the stream containing non-volatile particles through a light-scattering photometer. The light scattered by the non-volatile particles was collected and was a measurement of the concentration of the solute in the filter effluent. For the case of asphaltenes, the measurement of the light scattered also known as response represents the solubility characteristics of the asphaltenes present in the sample. Since the time scale can be converted to solubility parameter scale by using the regular solutions approach (Reference: Barton, A. F. M., Handbook of Solubility Parameters and other Cohesion Parameters, CRC Press, USA, 1991, p. 63), these curves represent the distribution of solubility parameters in the asphaltenes or solubility profile.

Figure 14:
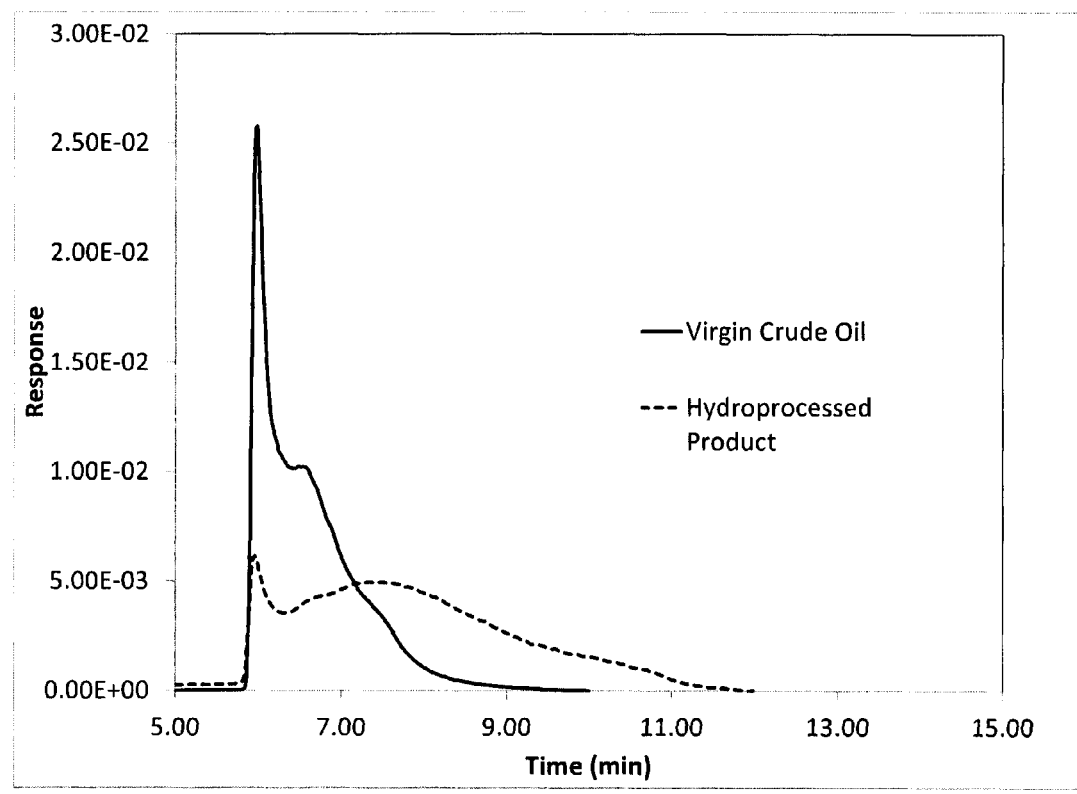
FIG. 14 shows the response for the asphaltenes for the different tested materials of Example 8.

FIG. 14 shows the response for the asphaltenes for both tested materials. This figure indicates the presence of two distinct features in each curve represented by separated peaks (hydroprocessed product) or a peak and a shoulder (Virgin crude oil). In both curves, the first peak corresponds to "easy to dissolve asphaltenes" and the second peak (or second shoulder) corresponds to "hard to dissolve asphaltenes".

The data in FIG. 14 confirms that asphaltenes from different hydrocarbon containing materials exhibit different solubility characteristics and that these differences can be measured by using method in-line filtration device.

EXAMPLE 9

Effect of temperature on asphaltene content.

A solution of asphaltenes (extracted from a heavy crude oil using ASTM D6560) was prepared by dissolving 0.0100 g of the material in 10 mL of methylene chloride. The solution was tested using Setup C, which consisted of a HPLC system composed of a HP Series 1100 chromatograph and a Dionex Corona ultra—charged aerosol detector (CAD). In addition, setup C uses a 0.5 micron filter suitable for HPLC and placed inside of an oven that can be setup at different temperatures.

Two experiments were conducted with filtration temperatures of 35° C. and 120° C., respectively. In this set of experiments, 4 microliters of solution were injected into the system using a heptane mobile phase at a flow rate of 1 mL/min with the filter at the desired temperature. After 8 min, the filter was cooled down to room temperature. Once the filter reached room temperature, the mobile phase was then switched to 90/10 methylene chloride/methanol blend at a flow rate of 1 mL/min and after 12 min, was switched back to 100% heptane at a flow rate of 1 mL/min. When the mobile phase was switched to 90/10 methylene chloride/methanol blend, asphaltenes started to elute and were quantified using the charged aerosol detector (CAD) by nebulizing the eluent, evaporating the solvent and charging the particles, passing the stream containing non-volatile particles (asphaltenes) through an electrometer. The charge was determined and was a measure of the concentration of the solute in the effluent.

Figure 15:
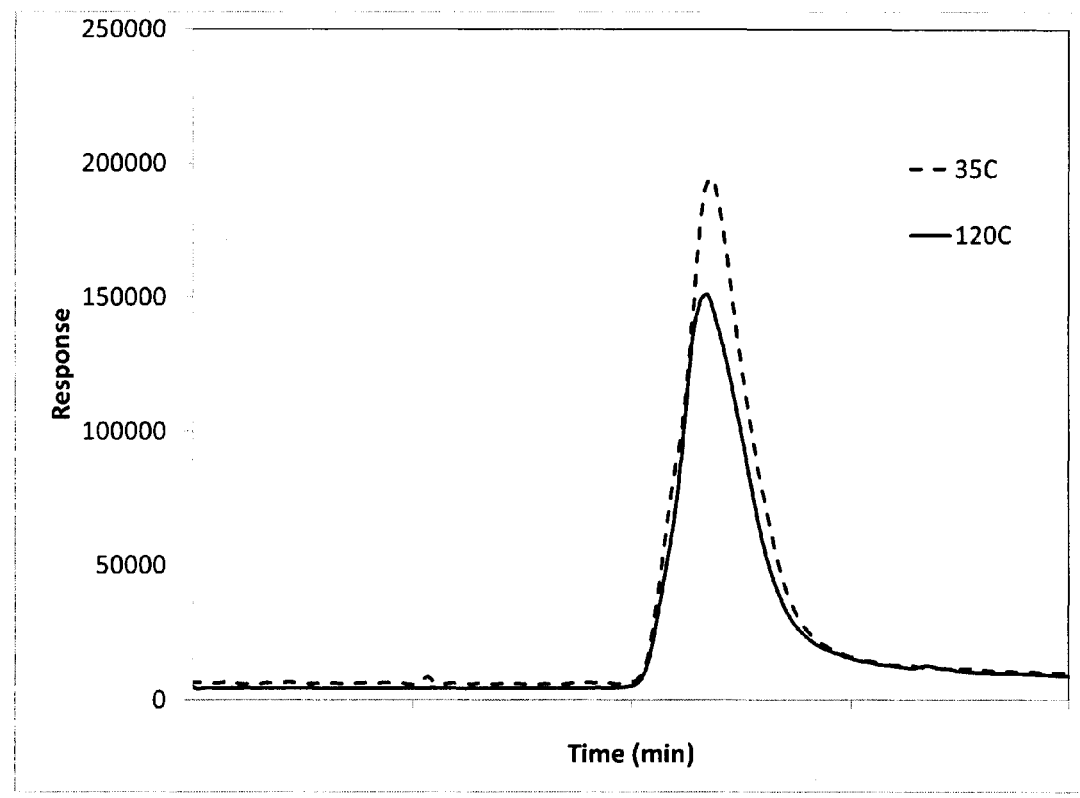
FIG. 15 shows the response for the asphaltenes obtained at different temperatures for Example 9.

FIG. 15 shows the response for the asphaltenes obtained at different temperatures. There was a decrease in the area of the asphaltene peak as the temperature increases and they become more soluble. The difference in the areas corresponds to a decrease of 25% in the amount of asphaltenes.

This set of experiments indicates that it is possible to determine the effect of temperature on asphaltene precipitation using a filtration device.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

What is claimed is:

1. A method for determining asphaltene stability in a hydrocarbon-containing sample having solvated asphaltenes therein, the method comprising the steps of:
   (a) precipitating an amount of the solvated asphaltenes from a liquid sample of the hydrocarbon-containing sample having the solvated asphaltenes therein with one or more first solvents and capturing precipitated asphaltenes in one or more low volume filters comprising a porous filter element comprising an area through which a fluid may flow, wherein the one or more low volume filters have a volume of less than 100 μL;
   (b) determining one or more solubility characteristics of the precipitated asphaltenes from step (a), wherein step (b) comprises either:
   (1)(i) dissolving at least part of a first amount of the precipitated asphaltenes from step (a) in one more second solvents having a solubility parameter at least about 0.7 MPa$^{0.5}$ higher then the solubility parameter of the one or more first solvents to provide a first eluted fraction with a first amount of the dissolved asphaltenes, and (1)(ii) dissolving a second amount of the precipitated asphaltenes from step (a) in one or more third solvents having a solubility parameter higher than the solubility parameter of the one or more second solvents, wherein the solubility parameter of the one or more third solvents is at least about 21 MPa$^{0.5}$ but no greater than about 30 MPa$^{0.5}$ to provide a second eluted fraction with a second amount of the dissolved asphaltenes; or (2) dissolving the first amount of the precipitated asphaltenes and the second amount of the precipitated asphaltenes from step (a) by gradually and continuously changing the one or more first solvents to a final mobile phase solvent having a solubility parameter at least about 1 MPa$^{0.5}$ higher than the solubility parameter of the one or more first solvents to provide an eluted fraction of the dissolved asphaltenes; and (c) analyzing the one or more solubility characteristics of the precipitated asphaltenes, which comprises monitoring either an amount of the first eluted fraction and the second eluted fraction from step (b)(1), or an amount of the eluted fraction from step (b)(2), from the one or more low volume filters with a liquid chromatography detector which generates a signal proportional to a concentration of the dissolved asphaltenes in either the first eluted fraction and the second eluted fraction from step (b)(1), or the eluted fraction from step (b)(2).

2. The method of claim 1, wherein the one or more low volume filters have the volume from about 1 μL to less than 100 μL.

3. The method of claim 1, wherein the one or more low volume filters have the volume from about 1 μL to about 10 μL.

4. The method of claim 1, wherein the one or more low volume filters are comprised of stainless steel, gold coated stainless steel, titanium coated stainless steel, silver plating coated stainless steel, carbon composite, or polyaryletherketones.

5. The method of claim 1, wherein the one or more low volume filters is capable of operating at a pressure up to about 15,000 psi and a temperature up to about 350° C.

6. The method of claim 1, wherein the porous filter element comprises a woven or a non-woven structure.

7. The method of claim 1, wherein the porous filter element has an average pore size lower than about 10 microns.

8. The method of claim 1, wherein the one or more low volume filters comprise two of the same or different low volume filters in series.

9. The method of claim 1, comprising calculating a percentage of each peak area for the first amount and the second amount of the dissolved asphaltenes from total peak areas, wherein peak areas are derived from signals.

10. The method of claim 1, further comprising the step of determining an asphaltene content of the liquid sample of the hydrocarbon-containing sample from the analyzing step (c).

11. The method of claim 10, wherein step (b) includes steps (b)(1)(i) and (b)(1)(ii), and further wherein the step of determining the asphaltene content comprises:

calculating a peak area for each of the amounts of the dissolved asphaltenes, wherein peak areas are derived from signals;

correlating the peak area to an asphaltene mass; and
adding each of the asphaltene masses (M) determined for each peak area to obtain a total asphaltene mass (TAM) according to the following equation:

$$TAM = \sum_{i=1}^{n} M_i$$

wherein M is the asphaltene mass determined for each peak area.

12. The method of claim 1, wherein step (b) includes steps (b)(1)(i) and (b)(1)(ii), and further comprising the step of determining one or more asphaltene stability parameters from the analyzing step (c), wherein the step of determining the one or more asphaltene stability parameters comprises (i) calculating a peak area for each of the amounts of the dissolved asphaltenes, wherein peak areas are derived from signals; and (ii) calculating a ratio of calculated peak areas for each eluted fraction according to the following equation:

Ratio=(area peak 3+area peak 4)/(area peak 1+area peak 2)

wherein area peak 1 is a first peak area characterizing the first eluted fraction eluted from the one or more low volume filters, area peak 2 is a second peak area characterizing the second eluted fraction eluted from the one or more low volume filters, area peak 3 is a third peak area characterizing the third eluted fraction eluted from the one or more low volume filters and area peak 4 is a fourth peak area characterizing the fourth eluted fraction eluted from the one or more low volume filters.

13. The method of claim 1, wherein step (b)(2) comprises:

(i) gradually and continuously changing the one or more first solvents to the final mobile phase solvent having a solubility parameter at least 1 MPa$^{0.5}$ higher than the solubility parameter of the one or more first solvents to dissolve the first amount of the precipitated asphaltenes to provide a first eluted fraction with the first amount of the dissolved asphaltenes; and (ii) gradually and continuously changing the first final mobile phase solvent to a second final mobile phase solvent having a solubility parameter at least 1 MPa$^{0.5}$ higher than the solubility parameter of the first final mobile phase solvent to dissolve the second amount of the precipitated asphaltenes to provide a second eluted fraction with the second amount of the dissolved asphaltenes.

14. The method of claim 13, further comprising the step of determining an asphaltene content from the analyzing step (c), wherein the step of determining the asphaltene content comprises:

calculating a peak area under an obtained second peak for the second amount of the dissolved asphaltenes, wherein the peak area is derived from the signal, correlating the peak area to an asphaltene mass; and determining a TAM in the liquid sample of the hydrocarbon-containing sample according to the following equation:

$$TAM = \sum_{i=1}^{n} M_i$$

wherein M is the asphaltene mass determined for each peak area.

15. The method of claim 13, further comprising the step of determining one or more asphaltene stability parameters comprising calculating an average solubility parameter of the second amount of the dissolved asphaltenes.

16. The method of claim 13, further comprising the step of determining one or more asphaltene stability parameters comprising calculating a ratio of peak areas of the second amount of the dissolved asphaltenes to the first amount of the dissolved asphaltenes, wherein each of the peak areas are derived from a solubility profile created from the dissolved asphaltenes.

17. The method of claim 16, wherein the step of determining the one or more asphaltene stability parameters comprises calculating an overlapping area of the peak areas of the second amount of the dissolved asphaltenes and the first amount of the dissolved asphaltenes.

18. The method of claim 13, further comprising the step of determining one or more asphaltene stability parameters comprising calculating an overlapping area of peak areas of the second amount of the dissolved asphaltenes and the first amount of the dissolved asphaltenes, wherein each of the peak areas are derived from a solubility profile created from the dissolved asphaltenes.

19. The method of claim 13, further comprising the step of determining one or more asphaltene stability parameters comprising calculating $\Delta PS$ from a $\Delta PS$ equation:

$$\Delta PS = t(75\%) - t(25\%)$$

wherein t(75%) and t(25%) represent a time at which 75% and 25% of the solvated asphaltenes in the liquid sample of the hydrocarbon-containing sample have eluted.

20. The method of claim 1, wherein in step (a) the precipitated asphaltenes are captured in the one or more low volume filters heated to an elevated temperature.

21. The method of claim 17, wherein the one or more low volume filters are heated to a temperature ranging from about 18° C. to about 350° C.

22. The method of claim 20, further comprising cooling the one or more low volume filters to room temperature prior to step (b), and wherein step (b) comprises dissolving at least part of the amount of the precipitated asphaltenes in the one or more second solvents having the solubility parameter at least about 0.7 MPa$^{0.5}$ higher than the solubility parameter of the one or more first solvents.

23. The method of claim 22, wherein the liquid chromatography detector in step (c) is an evaporative light scattering detector and step (c) further comprises nebulizing an eluted fraction sample thereby forming a multitude of droplets, the multitude of droplets comprising a solvent, asphaltene particles and non-asphaltene particles; evaporating the solvent from at least a portion of the multitude of droplets to thereby form a multitude of aerosol particles, wherein the multitude of aerosol particles comprise at least a second portion of the asphaltene particles and the non-asphaltene particles; charging at least a third portion of the non-asphaltene particles; and passing charged non-asphaltene particles through a charge-responsive device disposed to receive the charged non-asphaltene particles and determine a charge.

24. The method of claim 1, wherein step (b)(1), comprises
(i) dissolving at least part of the amount of the precipitated asphaltenes in the one or more second solvents having a dispersion solubility parameter at least about 0.4 MPa$^{0.5}$ higher then the dispersion solubility parameter of the one or more first solvents; and a total solubility parameter at least about 0.7 MPa$^{0.5}$ higher than the total solubility parameter of the one or more first solvents; and
(ii) dissolving the second amount of the precipitated asphaltenes in one or more third solvents having the dispersion solubility parameter at least about 1.5 MPa$^{0.5}$ higher than the dispersion solubility parameter of the one or more second solvents; and wherein the total solubility parameter of the one or more third solvents is at least about 17.8 MPa$^{0.5}$ but no greater than about 25 MPa$^{0.5}$.

25. The method of claim 24, comprising calculating a percentage of each peak area for the first amount and the second amount of the dissolved asphaltenes from total peak areas, wherein peak areas are derived from signals.

26. The method of claim 24, further comprising prior to step (ii):
dissolving at least part of the first amount of the precipitated asphaltenes in one or more fourth solvents having a dispersion solubility parameter between at least 0.4 MPa$^{0.5}$ higher then the dispersion solubility parameter of the one or more second solvents and the solubility parameter of the third solvent; and a total solubility parameter between the total solubility parameter of the one or more second solvents and the total solubility parameter of the third solvent; and
dissolving at least part of the second amount of the precipitated asphaltenes in one or more fifth solvents having a dispersion solubility parameter at least 0.8 MPa$^{0.5}$ higher than the dispersion solubility parameter of the one or more second sovents, and between the dispersion solubility parameter of a fourth solvent and the dispersion solubility parameter of the third solvent; and wherein the one or more fifth solvents have a total solubility parameter between the total solubility parameter of the fourth solvent and the total solubility parameter of the third solvent.

27. The method of claim 1, wherein step (b)(2) comprises:
(i) gradually and continuously changing the one or more first solvents to a first final mobile phase solvent having a dispersion solubility parameter at least about 2.0 MPa$^{0.5}$ higher than the dispersion solubility parameter of the one or more first solvents to dissolve the first amount of the precipitated asphaltenes; and a total solubility parameter at least about 2.0 MPa$^{0.5}$ higher than the total solubility parameter of the one or more first solvents; and
(ii) gradually and continuously changing the first final mobile phase solvent to a second final mobile phase solvent having the dispersion solubility parameter at least about 1 MPa$^{0.5}$ higher than the dispersion solubility parameter of the first final mobile phase solvent to dissolve the second amount of the precipitated asphaltenes, and wherein the second final mobile phase solvent has a total solubility parameter at least about 1 MPa$^{0.5}$ higher than the total solubility parameter of the first final mobile phase solvent.

28. The method of claim 27, comprising calculating a percentage of each peak area for each of the amounts of the dissolved asphaltenes from total peak areas, wherein peak areas are derived from signals.

* * * * *